(12) United States Patent
Schneider

(10) Patent No.: US 12,718,959 B2
(45) **Date of Patent: *Aug. 25, 2026**

(54) CODE FOR PATIENT CARE DEVICE CONFIGURATION

(71) Applicant: Baxter Corporation Englewood, Englewood, CO (US)

(72) Inventor: Dennis I. Schneider, Nashua, NH (US)

(73) Assignee: Baxter Corporation Englewood, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,473

(22) Filed: Feb. 5, 2024

(65) Prior Publication Data

US 2024/0177871 A1 May 30, 2024

Related U.S. Application Data

(63) Continuation of application No. 17/385,663, filed on Jul. 26, 2021, now Pat. No. 11,894,149, which is a (Continued)

(51) Int. Cl.
*G16H 70/40* (2018.01)
*G16H 20/17* (2018.01)
*G16H 40/63* (2018.01)

(52) U.S. Cl.
CPC ............ *G16H 70/40* (2018.01); *G16H 20/17* (2018.01); *G16H 40/63* (2018.01)

(58) Field of Classification Search
CPC ........ G16H 70/40; G16H 20/17; G16H 40/63; G16Z 99/00; G06Q 50/22
See application file for complete search history.

(56) References Cited

U.S. PATENT DOCUMENTS

| | | | | |
|---|---|---|---|---|
| 4,731,051 A | | 3/1988 | Fischell | |
| 8,234,128 B2 * | | 7/2012 | Martucci ............. | A61B 5/4839 705/2 |

(Continued)

FOREIGN PATENT DOCUMENTS

| | | |
|---|---|---|
| CN | 1497488 | 5/2004 |
| CN | 1702676 | 11/2005 |

(Continued)

OTHER PUBLICATIONS

James A. Eskew et al., Using Innovative Technologies to Set New Safety Standards for the Infusion of Intravenous Medications, Hospital Pharmacy vol. 37, No. 11, pp. 1179-1189 2002 Facts and Comparisons (Year: 2002).*

(Continued)

*Primary Examiner* — Joshua B Blanchette
(74) *Attorney, Agent, or Firm* — K&L Gates LLP

(57) ABSTRACT

A configuration output generator apparatus is disclosed herein. The configuration output generator apparatus is configured to receive a therapy order that includes a therapy description corresponding to a therapy to be administered by a patient care device to a patient. The configuration output generator apparatus generates a first portion of a configuration output from the therapy order. The first portion of the configuration output includes plain text values specifying a configuration protocol for preforming the therapy. The configuration output generator apparatus also generates, using an algorithm and the first portion of the configuration output, a second portion of the configuration output that comprises an alphanumeric code. The configuration output generator apparatus then outputs the first portion of the configuration output and second portion of the configuration output for entry into the patient care device.

16 Claims, 15 Drawing Sheets

Related U.S. Application Data continuation of application No. 14/765,897, filed as application No. PCT/US2013/032515 on Mar. 15, 2013, now Pat. No. 11,075,012.

(60) Provisional application No. 61/762,725, filed on Feb. 8, 2013.

(56) References Cited

U.S. PATENT DOCUMENTS

| | | | | |
|---|---|---|---|---|
| 2005/0144043 | A1* | 6/2005 | Holland ................. | G16H 70/40 705/3 |
| 2006/0047538 | A1* | 3/2006 | Condurso ............. | G16H 40/67 705/3 |
| 2006/0064053 | A1 | 3/2006 | Bollish et al. | |
| 2006/0122867 | A1 | 6/2006 | Eggers | |
| 2006/0229551 | A1* | 10/2006 | Martinez ................ | G16H 20/17 604/67 |
| 2007/0124002 | A1 | 5/2007 | Estes | |
| 2007/0213598 | A1 | 9/2007 | Howard et al. | |
| 2009/0177188 | A1 | 7/2009 | Steinkogler | |
| 2015/0371005 | A1 | 12/2015 | Schneider | |

FOREIGN PATENT DOCUMENTS

| | | |
|---|---|---|
| CN | 101073083 | 11/2007 |
| JP | 2010075606 | 4/2010 |
| RU | 2381038 | 10/2008 |
| WO | 02069099 | 9/2002 |
| WO | 2005031631 | 4/2005 |
| WO | 2005050526 | 6/2005 |

OTHER PUBLICATIONS

Yi Zhang et al., “A Hazard Analysis for a Generic Insulin Infusion Pump,” Journal of Diabetes Science and Technology, vol. 4, issue 2, Mar. 2010 (Year: 2010).*

Russian Office Action for Appl. No. 2015138124 (058476)—7 pages.

Russian Office Action for Appl. No. 2015138124 (058475)—English Translation—4 pages.

Indian Office Action for related Indian Application No. 6942/DELNP/2015 dated Apr. 29, 2020—6 pages.

Chinese Office Action and partial English translation for related Chinese application No. 201380074468.9 action dated Sep. 18, 2018; (16 pages).

Mexican Office Action for related Mexican Application No. MX/a/2015/010063; action dated Jul. 13, 2017—6 pages.

Chinese Office Action for related Chinese Application No. 201380074468.9; action dated Jan. 8, 2018—25 pages.

Search Report for Russian Application No. 2015138124 (058476)—English Translation—2 pages.

James A. Eskew et al., Using Innovative Technologies to Set New Safety Standards for the Infusion of Intravenous Medications, Hospital Pharmacy vol. 37, No. 11, pp. 1179-1189 2002 Facts and Comparison (Year: 2002).

Yi Zhang et al., “A Hazard Analysis for a Generic Insulin Infusion Pump,” Journal of Diabetes Science and Technology, vol. 4, Issue 2010, Mar. 2010 (Year: 2010).

* cited by examiner

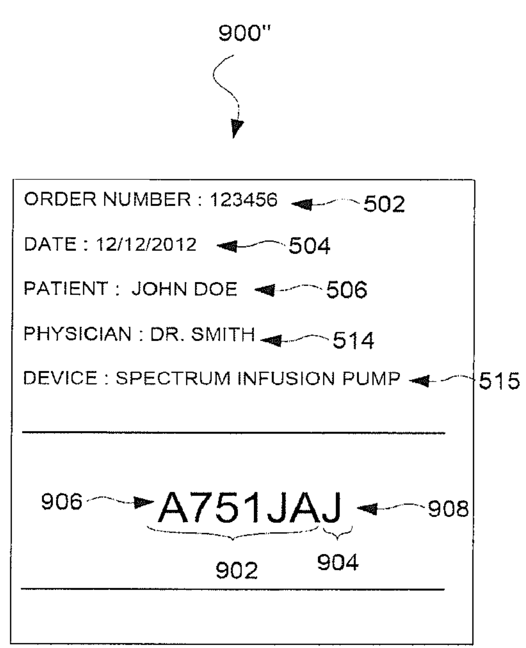

FIG. 11

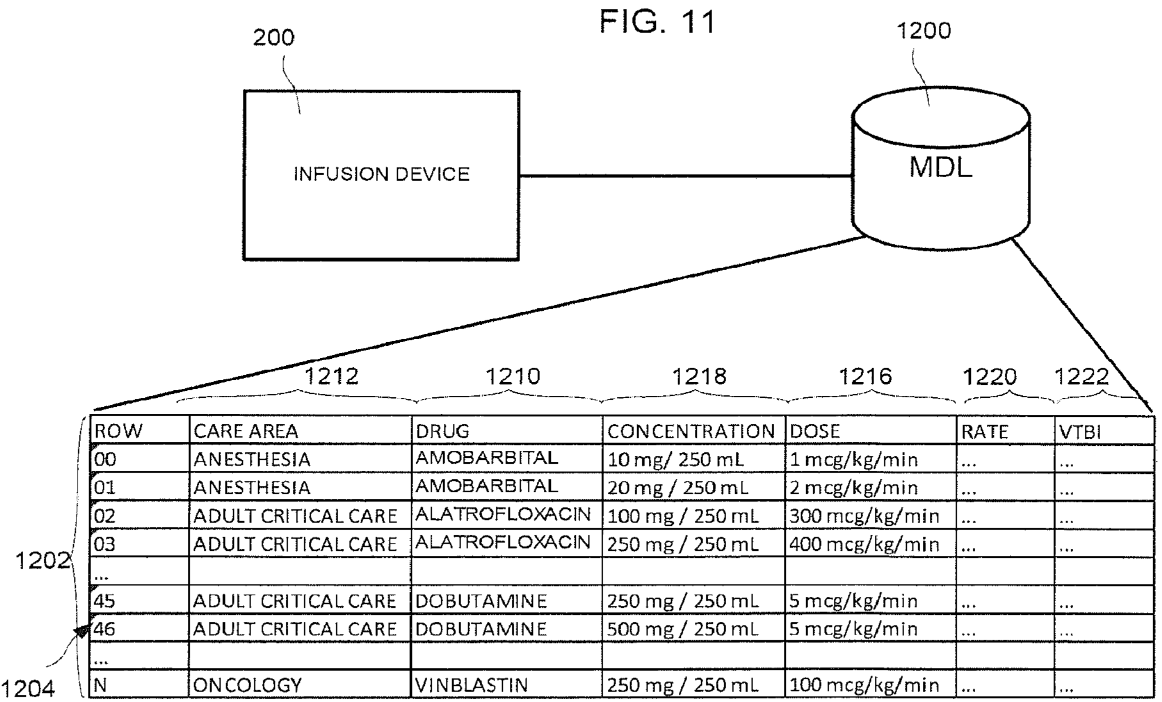

| ROW | CARE AREA | DRUG | CONCENTRATION | DOSE | RATE | VTBI |
|---|---|---|---|---|---|---|
| 00 | ANESTHESIA | AMOBARBITAL | 10 mg/ 250 mL | 1 mcg/kg/min | ... | ... |
| 01 | ANESTHESIA | AMOBARBITAL | 20 mg / 250 mL | 2 mcg/kg/min | ... | ... |
| 02 | ADULT CRITICAL CARE | ALATROFLOXACIN | 100 mg / 250 mL | 300 mcg/kg/min | ... | ... |
| 03 | ADULT CRITICAL CARE | ALATROFLOXACIN | 250 mg / 250 mL | 400 mcg/kg/min | ... | ... |
| ... | | | | | | |
| 45 | ADULT CRITICAL CARE | DOBUTAMINE | 250 mg / 250 mL | 5 mcg/kg/min | ... | ... |
| 46 | ADULT CRITICAL CARE | DOBUTAMINE | 500 mg / 250 mL | 5 mcg/kg/min | ... | ... |
| ... | | | | | | |
| N | ONCOLOGY | VINBLASTIN | 250 mg / 250 mL | 100 mcg/kg/min | ... | ... |

FIG. 12

CODE FOR PATIENT CARE DEVICE CONFIGURATION

PRIORITY CLAIM

This application is a continuation application of U.S. patent application Ser. No. 17/385,663, filed Jul. 26, 2021, entitled "CODE FOR PATIENT CARE DEVICE CONFIGURATION," now U.S. Pat. No. 11,894,149, which is a continuation application of U.S. patent application Ser. No. 14/765,897, filed Aug. 5, 2015, entitled "CODE FOR PATIENT CARE DEVICE CONFIGURATION," now U.S. Pat. No. 11,075,012, which is a national phase filing of PCT Patent Application No. PCT/US13/32515, filed Mar. 15, 2013, entitled "CODE FOR PATIENT CARE DEVICE CONFIGURATION," which claims priority to U.S. Provisional Patent Application No. 61/762,725 filed Feb. 8, 2013, entitled "CODE FOR PATIENT CARE DEVICE CONFIGURATION", the entire contents of each of which are hereby incorporated by reference and relied upon.

BACKGROUND

Information conveyance errors continue to represent a diverse and widespread challenge in the administration of medical therapies to patients. Specifically, errors may occur when a caregiver configures a patient care device based on instructions associated with a therapy to be administered to a given patient (e.g., when a caregiver inputs configuration data into the patient care device to establish operating parameters). In this context, errors may be introduced through a number of modalities including, for example, inaccurate data transcription, ineffective communication modalities, and/or inaccurate data conversion.

One such scenario where errors may be introduced is when a patient care infusion device is configured to administer an IV fluid corresponding to a dose order generated by a caregiver such as a physician. Given the nature of the therapy involved when administering IV fluids, errors in this context may result in patient harm. As such, the reduction of errors associated with the configuration of patient care devices, and in particular configurable infusion devices, continues to be of great importance

SUMMARY

The present disclosure is directed to the generation of a configuration output that may be used in connection with the configuration of a patient care device (e.g., a configurable infusion pump or similar apparatus) by a caregiver for administration of a medical therapy (e.g., infusion of a drug intravenously). As described herein, the configuration output may be generated to include a code that may be used when configuring a patient care device. In this regard, the use of a code may serve to reduce information conveyance errors associated with manually configuring a patient care device. The method according to this application may be a computer implemented method.

As noted above, in current practice, in configuring a patient care device a caregiver may be required to transcribe values from a given medium (e.g., a therapy order, a medical record, etc.) for entry in to the patient care device. In turn, the opportunity for errors may arise, e.g., transcription errors, entry of incorrect values, etc.

In some embodiments described herein, a code may be generated and used to verify the accuracy of one or more configuration data components that are input (e.g., manually by a human user) at a patient care device. In this regard, a verification code may be generated that is based, at least in part, on configuration data components that are intended for input into the patient care device. In turn, the verification code may be inputted to, and used at, the patient care device to detect whether the intended configuration data components are inputted accurately. Upon detection of an input error, the patient care device may be provided to alert the caregiver that an error has occurred so that the error may be rectified prior to initiation administration procedures. Advantageously, man machine interaction is improved, since a machine based verification of a user input is provided. In other words, the user may be relieved from and/or assisted in the mental task of verifying the input data. Therefore, configuration mistakes and/or incompatibilities can be reduced and/or detected.

Additionally or alternatively, in some embodiments described herein a code may be generated that is indicative of one or more configuration data components to be used in the configuration of a patient care device. In this regard, the patient care device may be provided so that entry of a code at the patient care device may be performed in lieu of manual entry of more extensive configuration data component(s) at the patient care device. For example, the patient care device may be provided with logic (e.g., prior to receipt of the code) to decipher an inputted code. The patient care device may utilize deciphered information from the code to obtain configuration data components for use in configuring the patient care device for administration of the therapy to a patient. In an implementation, the deciphered information may indicate pre-stored therapy data that is to be used to configure the patient care device for administration of the therapy. In an implementation, the deciphered information may itself comprise one or more configuration data components for use in configuring the patient care device. In either regard, the provided logic may include an appropriate algorithmic mechanism that is provided at the patient care device (e.g., prior to receipt of the code) to decipher the inputted code. Advantageously, man machine interaction is improved, since a machine based expansion of data that is e.g. manually input by a user, may be provided. In other words, the user only may input a relatively short code and may be relieved from and/or assisted in the mental task of memorizing and/or verifying lengthy and complicated input data. Therefore configuration mistakes and/or incompatibilities can be reduced or even avoided. This is even more the case, when inputting the code is machine aided, e.g. by a inputting the code as a bar code or other machine readable data and/or using a scanning and/or reader device.

In an embodiment, a code may be indicative of more than one configuration data component. The use of a code that is indicative of one or more configuration data components may reduce the number of data entry steps entailed for user configuration of a patient care device (e.g., reduce the number of key presses), thus reducing the potential for data entry errors, thereby improving man machine interaction.

In some implementations, regardless of whether the code is used to verify the accuracy of one or more entered configuration data components or is indicative of one or more configuration data components, the code may be checked to validate the accuracy of entry of the code. In this regard, a check code may be provided in the configuration output for use in validating the correct entry of the code. The check code may be integral to the code used to verify or indicate configuration data components (e.g., the code may be a self checking code including an integral check code feature) or may be a separate check code that is generated for use to validate the input accuracy of another code. Advantageously, man machine interaction is improved, since a machine based verification of input data is provided. In other words, the user is relieved from and/or assisted in the mental task of verifying the input data. Therefore, configuration mistakes and/or incompatibilities can be reduced and/or detected.

In view of the foregoing, in a first aspect, a method is provided for generation of a configuration output for a therapy order corresponding with a therapy to be administered to a patient using a patient care device. The method may include receiving a therapy order that includes a therapy description corresponding to a therapy to be administered to a patient and generating a configuration output for the therapy order for use in configuration of the patient care device for administration of the therapy. At least a first portion of the configuration output may include a first part that is at least partially generated based on a portion of the therapy description. Additionally, a second portion of the configuration output may include a first code that is at least partially generated based on the first portion.

A number of feature refinements and additional features are applicable to the first aspect. These feature refinements and additional features may be used individually or in any combination also with features of the second aspect described below. As such, each of the following features that will be discussed may be, but are not required to be, used with any other feature or combination of features of the first aspect.

In one embodiment, the first portion may be at least partially based on at least a portion of a configuration protocol of the patient care device. The configuration protocol comprises one or more configuration data input components (i.e., data values to be entered at the patient care device to configure the patient care device). The first portion may include data corresponding to one or more configuration data components to be used in the configuration of the patient care device. In this regard, the first portion may include plain text values corresponding to the configuration protocol of the patient care device. The plain text values may include values corresponding to configuration data components to be entered at the patient care device for configuration thereof. In this embodiment, the code of the second portion may include a verification code for verifying one or more entered values at the patient care device.

In some embodiments, the first portion may include a second code. In this regard, the second code may be at least partially generated based on a portion of the therapy description. In such embodiments, the first code may be at least partially generated based on the second code. As such, the first code may be used to verify the accuracy of entry of the second code at the patient care device. In turn, the second code may be used to indicate and/or verify one or more configuration data components for use in configuring the patient care device. Advantageously, man machine interaction is improved, since a machine based verification of input data by use of two codes may be provided. In other words, by providing and using two codes, machine based self-verification of input data may be established. Therefore, configuration mistakes and/or incompatibilities can be reduced and/or detected.

For example, in some implementations the first part of the first portion may include plain text values corresponding to the configuration protocol of the patient care device. As such, the plain text values may be read by an administrating caregiver to facilitate transcription of the values by the administrating caregiver to the patient care device. The first portion may also include a second part that includes the second code as described above.

In an embodiment, the second code may be indicative of the corresponding therapy description. In this regard, the second code may be indicative of a pre-stored therapy data set at the patient care device that corresponds to the corresponding therapy description. In turn, the second code may be used to direct the patient care device to access and retrieve pre-stored therapy data for use as configuration data components in the configuration of the patient care device. An example of this may be retrieving configuration data components from a master drug library (MDL) that correspond with a dose description for an IV fluid to be administered to a patient using a configurable infusion device. In an implementation, the code may be decipherable by the patient care device such that the patient care device may extract configuration data components directly from the code. Advantageously, a machine based retrieval of configuration data may be provided. Accordingly, the user is relieved from and/or assisted in the mental task of memorizing and/or inputting configuration data, so that the man machine interaction may be improved. In addition, advantageously, the patient care device can be configured based on a number of data component combinations for a number of different drug administrations in a machine verifiable manner.

In an embodiment, the first portion and the first code (e.g., in any permutation described above) may be entered at the patient care device by a user (e.g., including manual transcription and entry of the first portion and the first code by an administrating caregiver). For instance, the first portion may correspond to a configuration protocol of the patient care device, and the first code may be used at the patient care device to verify the first portion entered by the user. In an embodiment, the first portion may include a second code (e.g., as described above), and the first code may be used at the patient care device to validate the second code entered by the user.

In an embodiment, data corresponding to the therapy description may be an input for an algorithm utilized to generate the first code. Additionally, a corresponding algorithm may be stored at the patient care device. The corresponding algorithm may be operable to produce a comparison code for comparison to the first code for analysis of the first portion. Additionally or alternatively, the corresponding algorithm may be operable to decipher the first code for analysis of the first portion. Advantageously, man machine interaction is improved, since a machine based verification of the first code and/or the first portion may be carried out.

In an embodiment, a code (e.g., the second code) may be used as an identifier to track and/or manage therapy orders. For example, for a given therapy description, one of a plurality of predeterminable second codes may be generatable in the generating step. That is, a common therapy description (e.g., to be administered to different patients, at different times, etc.) may result in the generation of different predeterminable second codes. As such, each of the plurality of predeterminable second codes may be different. In this regard, each one of the plurality of predeterminable second codes may be generatable in corresponding relation to a different one of a plurality of time periods. That is, for a given one of the different plurality of time periods, each unique predeterminable second code may be generated only once. The plurality of time periods may correspond to a defined number of doses (e.g., a time period may be defined as the time in which a certain number of doses such as 5,000, 10,000, 15,000 etc., are received).

In any regard, during a given one of the plurality of time periods, one of the plurality of predeterminable second codes may be generatable in corresponding relation to a therapy order. Accordingly, the therapy order may correspond to a patient (i.e., the therapy order may be denoted as to be administered to a patient), and the one of the plurality of predeterminable second codes may be stored in corresponding relation to the patient. In this regard, the one of the plurality of predeterminable second codes may be receivable from the patient care device used to administer the therapy to the patient and data regarding the patient care device used to administer the therapy to the patient may be stored in corresponding relation with the patient. That is, one of the plurality of predeterminable second codes may be used to correlate a therapy order and/or a patient receiving the therapy order to an identity or other information regarding a patient care device used to administer the therapy. Advantageously, the functionality of the patient care device is adaptable to the needs of a specific patient that allows tracking of the therapy administered to the patient so that the user is relieved from and/or assisted in the mental task of tracking of the therapy administered to a patient.

In an embodiment, the method may also include identifying a patient care device to be used to administer the therapy to the patient, wherein the patient care device has at least one predetermined configuration protocol for therapy administration. As such, the first portion may be based at least in part on at least a portion of each of the therapy description and the predetermined configuration protocol. That is, in addition to including a code, the configuration output may be a patient care device-specific configuration output. As such, the first portion may at least partially correspond to one or more configuration data components of the predetermined configuration protocol, a data input sequence of the predetermined configuration protocol, and at least one configuration parameter form of the predetermined configuration protocol. In an embodiment, the configuration protocol may include at least one of the following types of data:

- data indicative of a location of the patient within a patient care facility;
- data indicative of one of a predetermined plurality of therapy types;
- data indicative of at least one drug;
- data indicative of therapy concentrations;
- data indicative of an administration rate;
- data indicative of an administration amount; or
- any other type of data.

In an embodiment, the generating step may be at least partially completed in a computer-automated manner. Furthermore, in an embodiment, the therapy may include administration of an IV fluid to a patient using an infusion device. The therapy order may include a dose order including a dose description corresponding to the IV fluid to be administered. The dose description may include one or more attributes of the IV fluid to be administered. In an embodiment, the method may include generating a label including the configuration output and affixing the label to a receptacle containing the IV fluid.

In an embodiment, at least one of (e.g., potentially both) of the first code and the second code may include one or more human-readable digits comprising an ASCII printable character. The first code and the second code may include one or more ASCII printable characters. For instance, the first code and the second code may include alpha-numeric codes.

According to an aspect, a computer program product is provided that can be stored on a computer readable medium and/or can be implemented as computer processable data stream, wherein the computer program product comprises computer processable instructions, which instructions when read in the memory of a computer and executed by the computer cause the computer to carry out the method(s) as described in general above, and in more specific examples below.

A second aspect includes a system for generation of a configuration output that includes an order entry interface that is operable to receive a therapy order that includes at least a portion of a therapy description corresponding to a therapy to be administered to a patient using a patient care device. The system also includes a configuration output generator in operative communication with the order entry interface and a configuration output that is generated by the configuration output generator. The configuration output includes a first portion that comprises a first part that is at least partially generated based on a portion of the therapy description and a second portion that comprises a second part that is at least partially generated based on the first portion.

A number of feature refinements and additional features are applicable to the second aspect. These feature refinements and additional features may be used individually or in any combination also with features of the first aspect described above. As such, each of the following features that will be discussed may be, but are not required to be, used with any other feature or combination of features of the second aspect.

In an embodiment, the system may include a patient care device having a user interface for receipt of the first portion and the second portion by way of manual entry by a user. Furthermore, the therapy may include administration of an IV fluid to a patient using the patient care device. The patient care device may be an infusion pump. The therapy order may include a dose order including a dose description corresponding to the IV fluid to be administered using the infusion pump. Additionally, the configuration output may be a label. In turn, the label may be applied to a receptacle containing the IV fluid.

In various embodiments, a patient care device may be configurable and/or otherwise provided with logic to determine whether or not a code as described herein is required to configure the patient care device for a given intended operation. For example, a patient care device may be provided so that input of a code, as discussed herein, is required in some uses, and not required in other uses, of the patient care device.

The configuration output generator, the patient care device, and/or other portions of the system according to the first aspect may be operable to perform functionality associated with any or all of the method of the first aspect and variations thereof as described above. As such, it may be appreciated that any of the discussion above regarding the method of the first aspect may be carried out by the system of the second aspect without limitation.

BRIEF DESCRIPTION OF THE FIGURES

FIG. 11 depicts an embodiment of a configuration output with a code corresponding to the dose description of FIG. 4 that is indicative of one or more configuration data component inputs corresponding to the dose description and a check code for validation of the code.

FIG. 12 depicts an embodiment of pre-stored therapy data that may be indicated for use in configuration of a patient care device.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
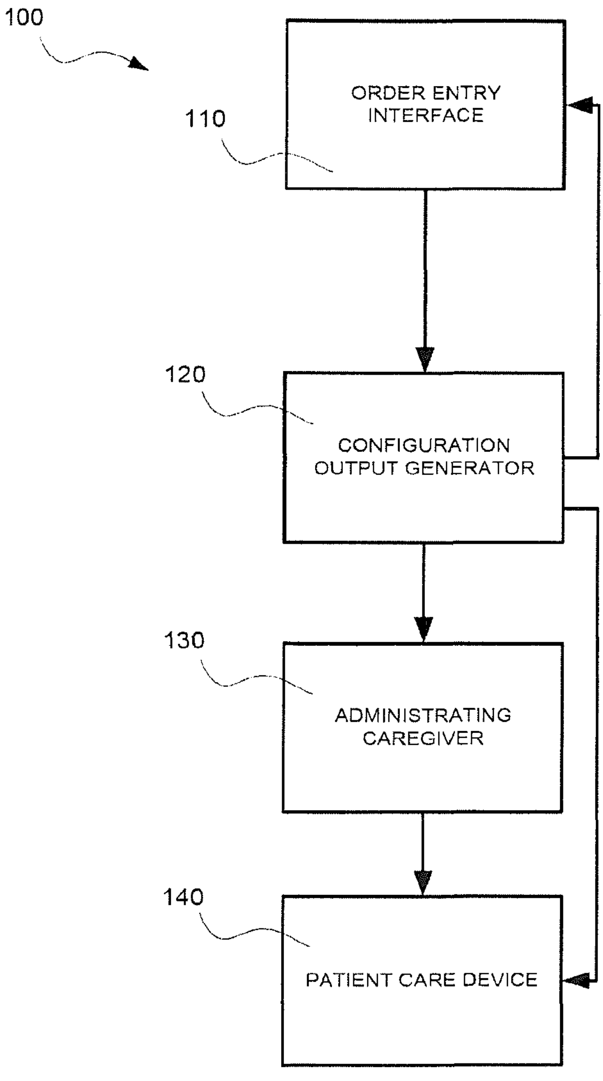
FIG. 1 is a schematic representation of an embodiment of a work flow for configuration of a patient care device to administer an ordered therapy to a patient using a patient care device.

FIG. 1 depicts a schematic representation of an embodiment of a work flow 100 that facilitates generation of a configuration output for use in configuration of a patient care device 140. The configuration output may be a patient care device-specific configuration output and/or may include a code. As such, the following disclosure initially generally discusses the work flow 100 that may be used to generate either a patient care device-specific configuration output and/or a configuration output having a code. In turn, embodiments of a patient care device-specific configuration output are presented. Thereafter, embodiments related to a configuration output including a code are described.

Generally, the work flow 100 may include use of an order entry interface 110 for receiving an order for a therapy that is to be administered to a patient using the configurable patient care device 140. The order entry interface 110 may output data corresponding to a therapy order for receipt by a configuration output generator 120. The configuration output may be provided to an administrating caregiver 130. The administrating caregiver 130 may then use the configuration output received from the configuration output generator 120 to configure the patient care device 140. As may be appreciated in the discussion below regarding the various embodiments of configuration outputs, the use of the configuration output to configure a patient care device may assist in reduction of configuration errors. Additionally or alternatively, the configuration output generator 120 may provide the configuration output directly to the patient care device 140 (e.g., for display or other use of the configuration output at the patient care device 140). This may be accomplished through any known or not yet known communication means including any wired, wireless, or other communication means. Further, as shown, and as will be discussed in greater detail below, the work flow 100 may include a feedback loop between the configuration output generator 120 and the order entry interface 110 that may be used to solicit additional information regarding the order (e.g., once the order is analyzed by the configuration output generator 120).

The order entry interface 110 may comprise a computer-based order entry system. That is, the order entry interface 110 may include a graphical user interface (GUI) facilitated by a computing device that allows a caregiver to enter information corresponding to an order for administration to a patient. For example, the computing device may be a networked computing device such as a personal computer, network terminal, mobile device, or other computing device. In this regard, the order entry interface 110 may include at least one processor operable to access a memory storing instructions to control execution of the processor to receive and output an order.

Figure 2:
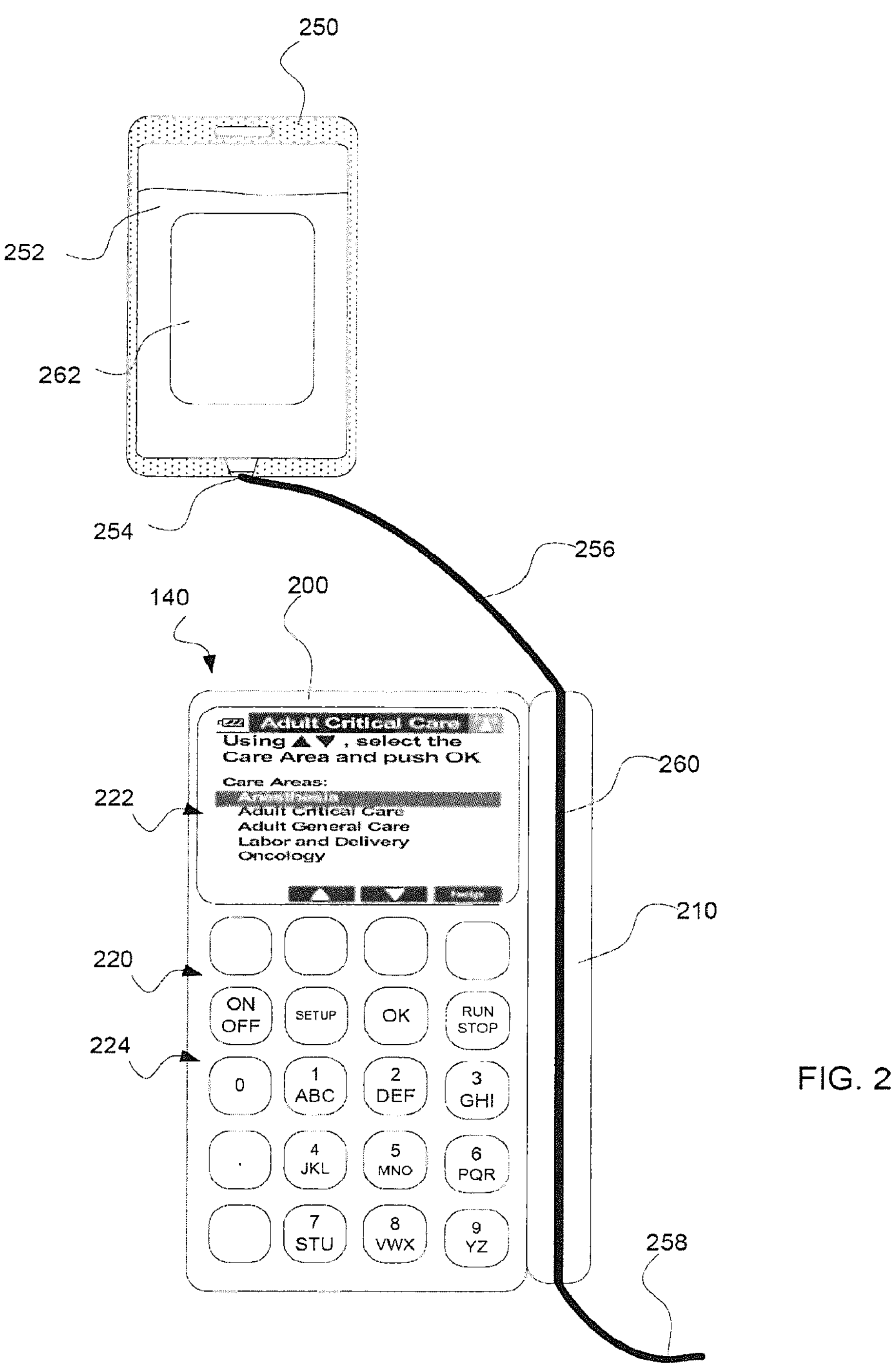
FIG. 2 represents an embodiment of a configurable patient care device comprising a configurable infusion device that is in operative engagement with an IV fluid contained in a receptacle for administration to a patient.

In any regard, the order entry interface 110 may receive information from a caregiver regarding a therapy to be administered to a patient. In an embodiment, the therapy may include the administration of an IV fluid to a patient using a configurable patient care device 140. For example, as depicted in FIG. 2, the configurable patient care device 140 may include an infusion device 200 (e.g., a configurable infusion pump). In this regard, the order received at the order entry interface 110 may be a dose order with dose information corresponding to an IV fluid 252 to be administered to a patient. In this regard, the dose information may include one or more attributes of the IV fluid and/or the administration thereof. The IV fluid 252 to be administered to the patent may be contained by a receptacle 250. The receptacle 250 may include an administration port 254 that facilitates connection of an administration set 256 to the receptacle 250. The administration set 256 may be used to facilitate fluid communication between the receptacle 250 and a patient (not shown) at a distal end 258 of the administration set 256.

Additionally, a portion 260 of the administration set 256 may be disposed within a pump portion 210 of the infusion device 200. In this regard, the pump portion 210 may have an appropriate mechanism (e.g., a peristaltic pump device) for control of the flow of the IV fluid 252 through the administration set 256 for administration of the IV fluid 252 to the patient. Other appropriate types of infusion devices

200 may be provided that allow for control of the administration of an IV fluid 252 to a patient.

In this regard, the infusion device 200 may be configurable to control the pump portion 210 for controlled administration of the IV fluid 252 to the patient. For example, the infusion device 200 may include a graphical user interface (GUI) 220 used to receive configuration instructions (e.g., including one or more configuration data components) from an administering caregiver 130. The GUI 220 may include a display 222 and an input device 224 (e.g., including a plurality of buttons or keys as shown in FIG. 2). Other input devices 224 may be provided including for example, a touch screen input device, a keyboard, or other human-machine interface. In this regard, the administering caregiver 130 may use the input device 224 to input one or more configuration data components regarding the ordered administration of the IV fluid 252 to the patient that is in turn reflected on the display 222.

Furthermore, even if the order data is included on the label 262 disposed on the receptacle 250, there may still be incorrect, missing, or misidentified data. For example, the data appearing on the label 262 may require the administering care giver 130 to perform conversions or provide supplemental data to arrive at the necessary configuration data component input for configuring the patient care device 140. Therefore, in addition to the errors identified above, the potential for errors on the part of the administering caregiver 130 may include mathematical errors, unit of measure conversion errors, or other errors introduced when the administering caregiver 130 attempts to configure the patient care device 140 in accordance with the order. As may be appreciated from the following discussions regarding patient care device-specific configuration outputs and configuration outputs including a code, either or both approaches to configuration outputs may assist in reduction of errors associated with the configuring of a patient care device.

Figure 3:
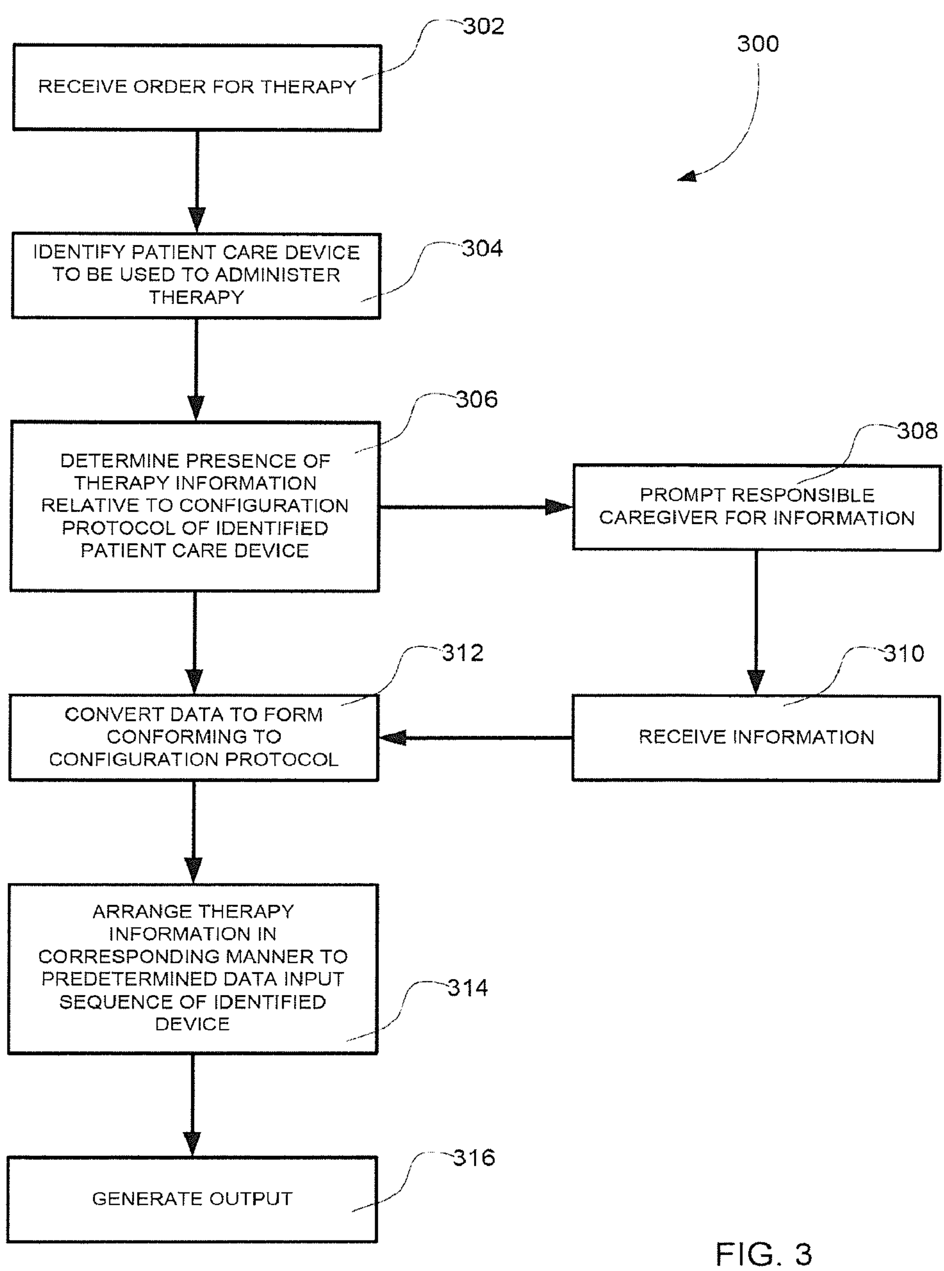
FIG. 3 depicts a flow chart corresponding to an embodiment of a method for generation of a patient care device-specific configuration output for an order.

Accordingly, in an embodiment, the configuration output may be a patient care device-specific configuration output. In this regard, the configuration output may correspond to an identified patient care device 140 for administration of the ordered therapy to the patient. That is, the configuration output may be at least partially generated based on a therapy order and the identified patient care device 140. For example, the configuration output generator 120 may generally perform a method 300 as shown in FIG. 3. In this regard, the configuration output generator 120 may comprise hardware, software, or combinations thereof. For example, in an embodiment, the configuration output generator 120 may at least comprise a general purpose processor and a memory. Further, instructions corresponding to the method 300 as described below may be provided in the form of non-transitory machine-readable data that is accessible by the processor to control the operation thereof to perform the method 300 described below. As such, the configuration output generator 120 may include or be executed on a computing device such as a networked computing device, a network terminal, a mobile device, or other appropriate computing device. Additionally or alternatively, at least portions of the method 300 may be performed by application specific integrated circuits (ASICs), field gate arrays (FGAs), or other appropriate devices for executing functionality as will be appreciated by one of ordinary skill in the art. Accordingly, any or all steps of the method 300 may be performed in a computer-automated manner.

The method 300 may include receiving 302 an order for a therapy. For example, the therapy order may be received via an order entry interface 110 as referenced in FIG. 1. Once the therapy order is received 302, the method 300 may include identifying 304 the patient care device 140 to be used to administer the ordered therapy to the patient. In this regard, the identifying 304 may include identifying one of a plurality of types of devices that may be used in the administration of the therapy to the patient. Each type of device may include a different predetermined configuration protocol. For example, in the case of a configurable infusion device 200 as described in FIG. 2, a facility may have more than one type of infusion device. Each of the different types of infusion devices 200 may have a predetermined configuration protocol that differs with respect to each other type of infusion device 200. In this regard, the identifying may include, rather than identifying a specific one of patient care devices 140 of a facility to be used to administer a therapy, a type of patient care device 140 may be determined such that the predetermined configuration protocol is determined for the device 140 to be used in the administration of the ordered therapy.

In another embodiment described in greater detail below, the identifying step 304 may include selecting or assigning a patient care device 140 at least partially based on the therapy order. For example, in the context of a dose order, the assigning of an appropriate infusion device 200 may be based upon the type of infusion, the identity of the drug to be infused, the patient to whom the IV fluid is to be administered, the current location of the patient, or any other factor. In an embodiment, the identifying 304 is based on the current location of the patient and the identity of the drug to be infused. Once this information is known, an appropriate infusion device 200 may be selected such that the configuration protocol thereof is known. In any regard, once the predetermined configuration protocol for a patient care device 140 to be used to administer the therapy has been identified 304, then information corresponding to the therapy order may be analyzed and/or processed to output a configuration output based on at least a portion of the information regarding the therapy order and the identification of the patient care device 140.

For example, as shown in FIG. 3, an embodiment of method 300 may include determining 306 the presence of information in the therapy order that corresponds to the configuration protocol of the identified patient care device 140. For example, the configuration protocol may include one or more configuration data components used to configure the patient care device 140. Therefore, in a particular scenario, it may be determined that a portion of the information corresponding to one or more of the configuration data components used in the configuration of the patient care device 140 is not provided in the therapy order. Furthermore, a scenario may exist where the therapy order includes conflicting information corresponding to one or more of the configuration data components used in the administration of the therapy. Other scenarios may be provided for where there is some deficiency in the information provided in the order. In any regard, the method 300 may include prompting 308 a responsible caregiver for information. This may include alerting a responsible caregiver of the issue (e.g., via the order entry interface 110) and may include prompting the responsible caregiver for additional information from the caregiver regarding the ordered therapy (e.g., for a missing data component or for clarification concerning conflicting data components). In another embodiment, information may be solicited from a responsible care giver (e.g., a pharmacist, nurse, etc.) via a mechanism other than the order entry interface 110 such as, for example, a pharmacy management system, an electronic medical records system, or other appropriate interface.

The prompting 308 may include soliciting additional information regarding the therapy order, requesting clarification of conflicting information, or otherwise requesting information needed to prepare a configuration output corresponding to the therapy order. Accordingly, the method 300 may include receiving 310 information from the responsible caregiver. In an embodiment, the receiving 310 of the information may be required prior to generation 316 of the configuration output. In this regard, prior to the generation 316 of the configuration order, all information needed to configure the patient care device 140 may be obtained. Thus, a scenario where an administrating care giver 130 attempts to enter values from memory, guess at values, or otherwise improvise based on a lack of configuration data components in the configuration output may be avoided.

The method 300 may also include converting 312 data to a form conforming to the configuration protocol. The form of configuration data components may correspond to a number of attributes such as, for example, units of measure, use of abbreviations, nomenclature, etc. In this regard, the converting 312 may include modification of information from the therapy order to a form that corresponds directly to the configuration protocol of the identified patient care device 140. For example, a portion of the therapy information may include information described in units of measure different than the unit of measure designation used in the configuration protocol. Traditionally, an administering caregiver 130 may be required to perform such a conversion manually to correct for the discrepancy between the units of measure of the order and the units of measure used in the configuration protocol of the patient care device 140. As may be appreciated, such manual conversions may be prone to errors. Additionally, different nomenclature used between the therapy order and the configuration protocol may result in the administrating caregiver becoming confused or mistranscribing data. However, the configuration output generator 120 may be operable to automatically perform the converting 312 such that data appearing in the resulting configuration output conforms to the form of the configuration protocol. Other examples of converting 312 the form of information are discussed in greater detail below with respect to FIGS. 4 and 5.

The method 300 may also include arranging 314 the information in the configuration output to correspond to a data input sequence of the configuration protocol. That is, the configuration protocol may have a sequence of data inputs (e.g., corresponding to the sequence of input of configuration data components of the configuration protocol) that are provided in a specific order. The therapy order may have at least a portion of information that is not arranged corresponding to the data input sequence of the configuration protocol. Therefore, in a traditional approach, an administering caregiver 130 may be required to search the therapy order to find the appropriate therapy information from a plurality of potential locations of the therapy order and/or from the therapy order in an order different than the data input sequence of the configuration protocol. As may be appreciated, this may result in the administering caregiver 130 misreading, entering the therapy information in a sequence that does not correspond to the data input sequence of the configuration protocol, entering therapy information from memory, or otherwise erring, thus resulting in the input of incorrect values. However, in the method 300, as the information in the configuration output may be arranged in correspondence with the data input sequence of the configuration protocol, the administering caregiver 130 may be able to sequentially enter the information for the configuration protocol in a manner that allows the caregiver to simply follow the data input sequence of the configuration output. This may assist the administrating caregiver 130 in accurately and precisely transcribing values from the configuration output to the patient care device 140.

Additionally, the method 300 may include generating 316 the configuration output. The generating 316 may include preparing the configuration output in any appropriate form, whether printed, electronic, or otherwise. As will be appreciated with further regard to the discussion below regarding a configuration output including a code, the generation of a configuration output that follows may be applicable to any configuration output described herein. In this regard, the generating 316 may include generation of the configuration output on a display (i.e., preparing a soft copy of the configuration order), generating a hard copy of the configuration output, and/or preparing the configuration output as machine-readable data and/or generating the configuration output in an electronic format for electronic transmission by any communication means. As described above, the configuration output may be communicated to the patient care device 140. In this regard, the soft copy output of the configuration output may be displayed at the patient care device 140.

In an embodiment, the generating 316 may include printing a label that may be associated with an object used in the administration of the ordered therapy. For example, as will be described in greater detail below, in the context of an IV fluid 252 to be administered using an infusion device 200, the label 262' may be attached to a receptacle 250 for the IV fluid 252 (see, e.g., FIG. 6). As such, the label 262' may include a patient care device-specific configuration output and/or a configuration output including a code. Further still, the generating 316 may include preparing machine-readable data in an appropriate format for distribution to and/or use directly by the patient care device 140. In this regard, the generating 316 may include generation of computer-readable data that may be provided directly to a patient care device 140 for configuration the patient care device 140.

As referenced above, the method 300 of FIG. 3 may be utilized in the context of preparing a configuration output for the administration of an IV fluid 252 to a patient using an infusion device 200. With reference to FIGS. 4-7E, one such example is described hereinbelow. For example, in FIG. 4, a dose order 400 corresponding to an ordered dose (e.g., an IV fluid) to be administered to a patient may be received. It may be appreciated that the dose order 400 may be in the form of data stored in memory. Therefore, the display of the dose order 400 in FIG. 4 in human-readable form may be for illustration purposes.

Figures 4, 5:
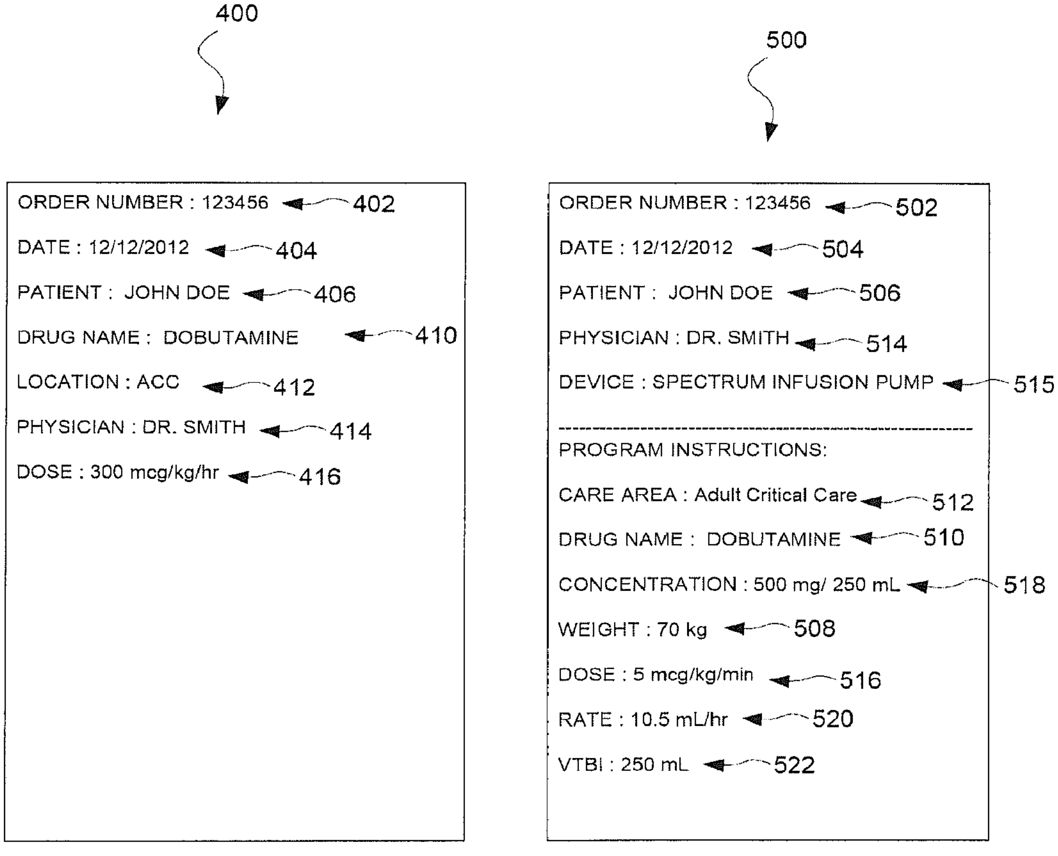
FIG. 4 represents an embodiment of a dose order corresponding to an IV fluid to be administered to a patient.
FIG. 5 represents an embodiment of a patient care device-specific configuration output corresponding to the dose order of FIG. 4.

As shown in FIG. 4, the dose order 400 may include a plurality of portions of dose information. These portions of dose information may include attributes of the IV fluid 252 and/or the administration thereof. In this regard, while the portions of dose information in FIG. 4 include an order number 402, an order date 404, a patient name 406, a drug name 410, a patient location 412, an ordering physician 414, and a dose amount 416, it may be appreciated that fewer or additional portions of information may be provided with a dose order 400 and that the specific portions shown in FIG. 4 are for explanation purposes and are not intended to be limiting. Therefore, other portions of information (e.g., including additional attributes of the IV fluid to be administered) may be provided without limitation.

A configuration output generator 120 may receive the dose order 400 and generate a patient care device-specific configuration output 500 (e.g., according to method 300). In this regard, it may be determined that the IV fluid 252 corresponding to the dose order 400 is to be administered by an infusion device 200 of the type shown in FIGS. 7A-7E. In this regard, FIGS. 7A-7E may depict an embodiment of a predetermined configuration protocol for the infusion device 200. The predetermined configuration protocol of the infusion device 200 may further have a particular data input sequence in which the various configuration data components for configuring the infusion device 200 are requested from a user. As such, in FIGS. 7A-7E each successive figure may represent a subsequent GUI 220 state in the data input sequence for receiving configuration data components of the predetermined configuration protocol for configuring the infusion device 200. In this regard, the configuration output 500 shown in FIG. 5 may be generated based on the dose order 400 and the identification of the infusion device 200 as the patient care device to be used to administer the IV fluid 252 described by the dose order 400. As may be appreciated, some portions of the dose information from FIG. 4 may be carried over to the patient care device-specific configuration output 500 such as the order number 502, order date 504, patient name 506, and ordering physician 514. Additional information may also be supplemented, such as, for example, the device type 515 to be used to administer the therapy.

Figure 6:
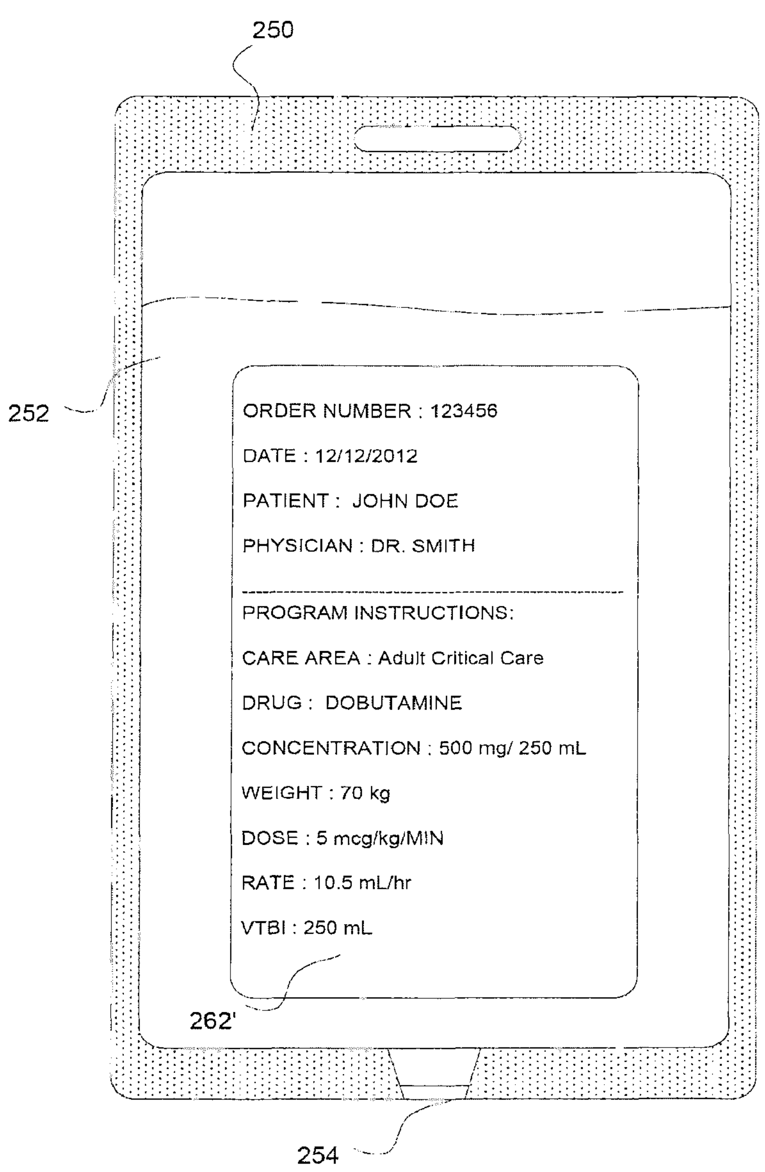
FIG. 6 depicts an embodiment of a configuration output comprising a label applied to a receptacle for an IV fluid to be administered to a patient.

Furthermore, as shown in FIG. 6, the configuration output 500 may comprise a label 262' that is applied to the receptacle 250 for the IV fluid 252 to be administered. As may be appreciated with respect to FIGS. 9-11 below, the configuration outputs 900, 900', and 900" discussed in greater detail below could also be applied to a receptacle 250 as shown in FIG. 6. In any regard, the IV fluid 252 may be a compounded IV fluid admixture that is prepared by a pharmacy. The pharmacy may also include the configuration output generator 120 such that the configuration output 500 is generated substantially concurrently with the preparation of the IV fluid 252. Thus, once the IV fluid 252 has been prepared and disposed in the receptacle 250, the configuration output 500 may be applied in the form of the label 262' to the receptacle 250 for the IV fluid 252. In this regard, the label 262' may be an adhesive backed label that is applied to the receptacle 250 prior to the dispensation of the receptacle 250 from the pharmacy. As such, the receptacle 250 including the IV fluid 252 and the configuration output 500 may be collectively delivered to an administering caregiver 130 for subsequent administration to a patient.

Figure 7A:
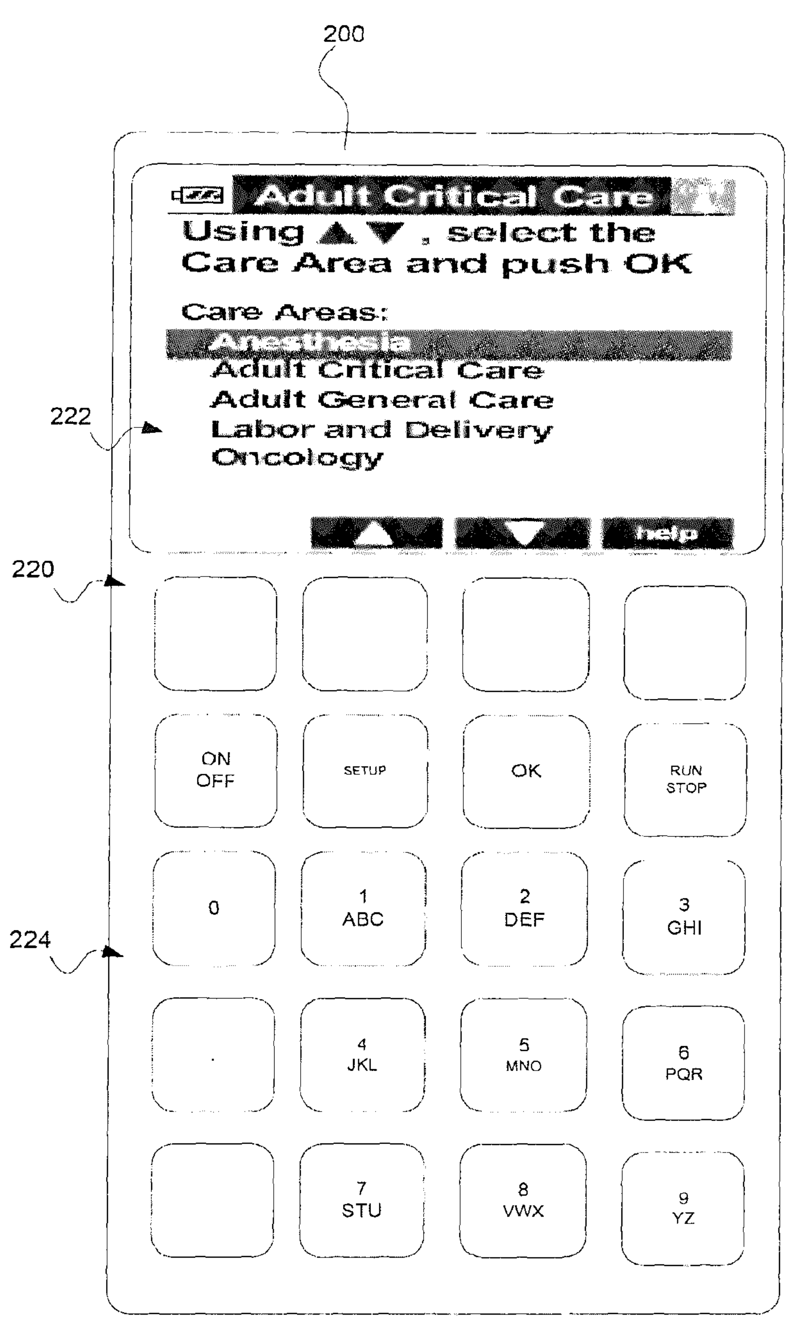
FIGS. 7A-7E depict an embodiment of a user interface of a configurable infusion device in plurality of different states corresponding a configuration protocol for configuring the infusion device.

Accordingly, at the initiation of the configuration protocol as shown in FIG. 7A, the configuration protocol may include selection of a care area in which the IV fluid 252 is to be administered (e.g., which may correspond to a patient location in a care facility). As may be appreciated, the dose order 400 may include a patient location 412. In this regard, with further reference to FIG. 5, the information associated with the patient location 412 may be modified for inclusion in a corresponding care area data field 512 in the configuration output 500. For example, rather than being designated as a "LOCATION" as per the dose order 400, the configuration output 500 may modify the listing of the patient location information 412 to be designated as a "CARE AREA" in the care area data field 512 that corresponds to the requested input as shown in FIG. 7A. In this regard, the form of the patient location information 412 may be modified in this respect. Furthermore, the patient location 412 may be abbreviated as "ACC" in the dose order 400. In the care area data field 512 of the configuration output 500 the value may be converted to "Adult Critical Care" to correspond to the specific input shown in the display 222 of the GUI 220 as shown in FIG. 7A, this is further modifying the form of the patient location information 412. In this regard, the administering caregiver 130 may use the GUI 220 of the infusion device 200 to select "Adult Critical Care". The selection of the care area may result in the GUI 220 changing to the state shown in FIG. 7B (e.g., advancing the data input sequence of the configuration protocol).

Figure 7B:
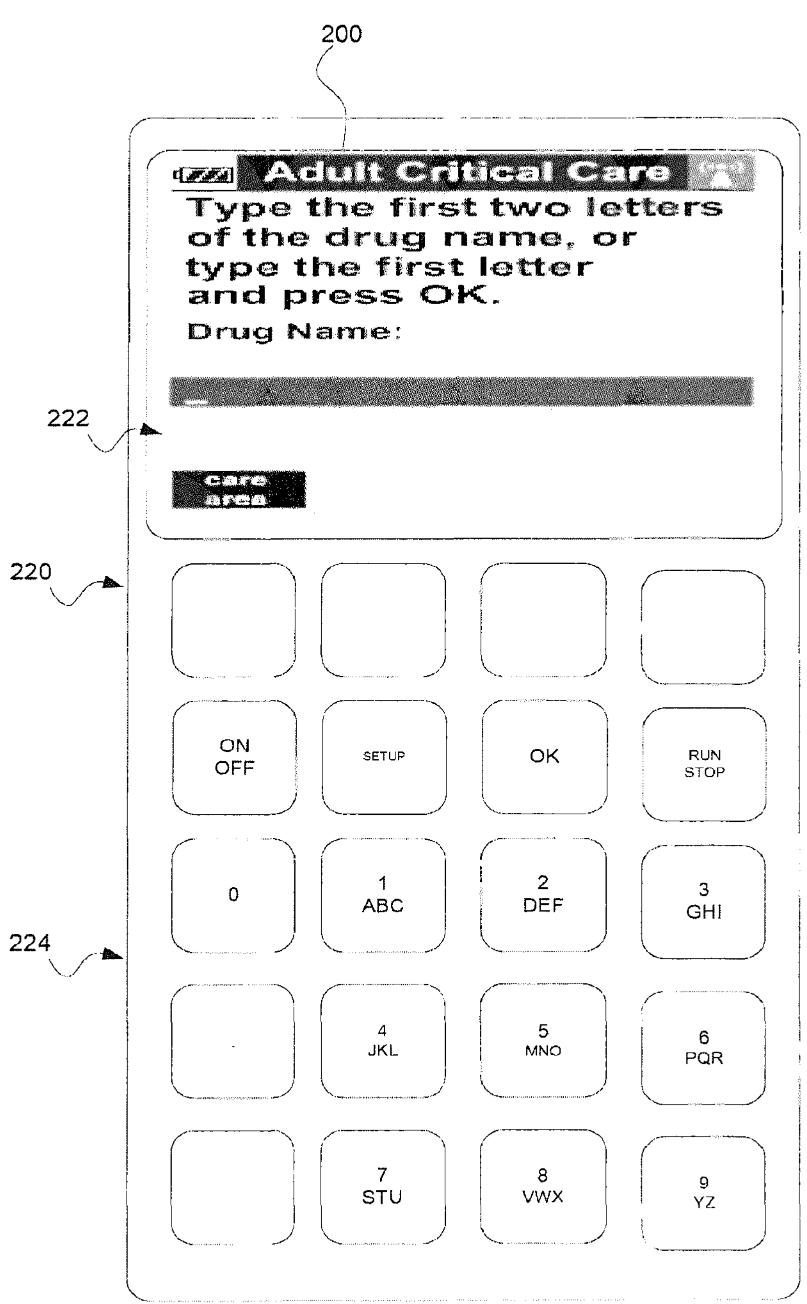
Figure 7C:
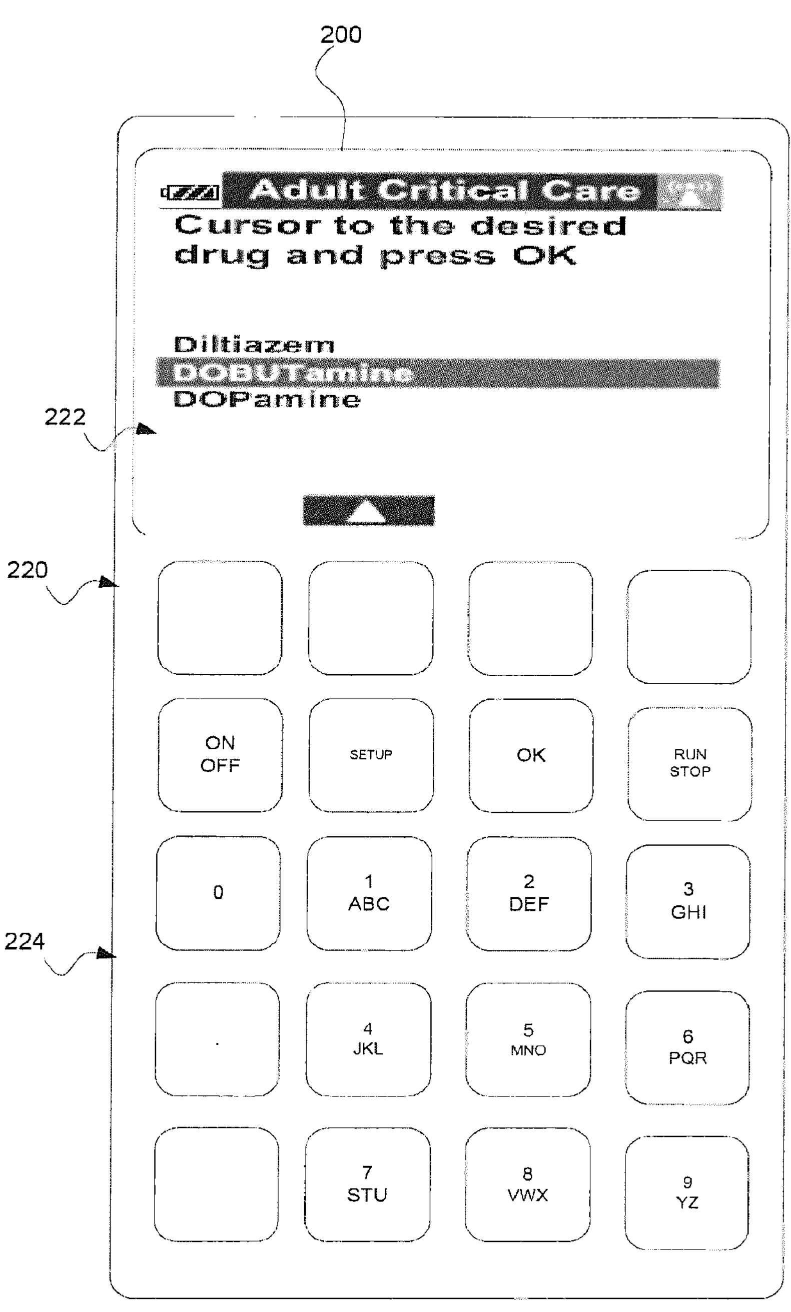

In FIG. 7B, the GUI 220 may prompt the administering caregiver 130 for the name of the drug to be administered. The drug name 412 from the dose order 400 may be included in the configuration output 500. As can be appreciated in FIG. 5, the drug name information 512 may appear directly sequentially after the patient location information 512 such that the arrangement of the care area 512 and the drug name 510 correspond to the data input sequence of configuration protocol for the infusion device 200. It should be noted that such an arrangement may differ from that of the dose order 400. In this regard, the administering caregiver 130 may use the input device 224 to enter the drug name as shown in FIG. 7C based upon the drug name 510 provided on the configuration output 500. Upon selection of the drug to be administered, the GUI 220 may change to the state shown in FIG. 7D (e.g., advancing the data input sequence of the configuration protocol).

Figure 7D:
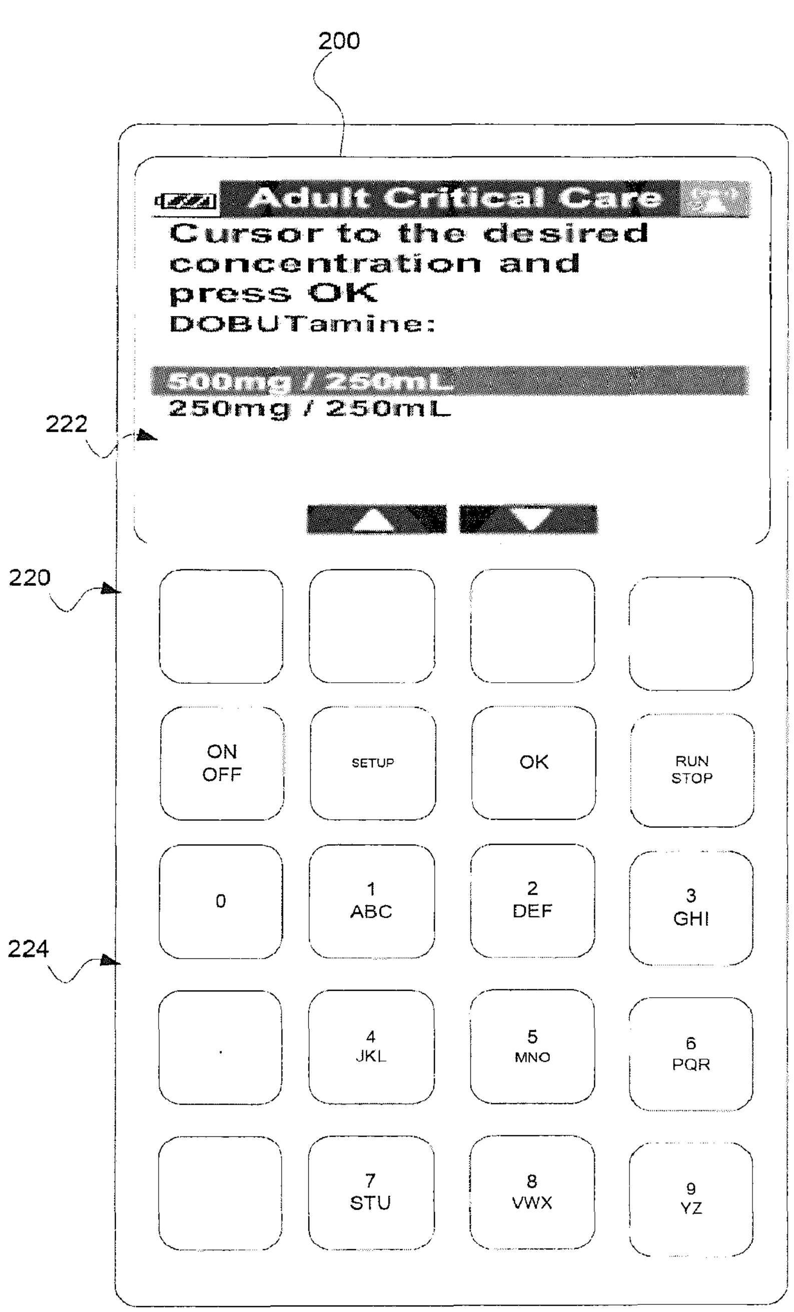

In FIG. 7D, the concentration of the drug to be administered at the infusion device 200 is to be selected via the GUI 200. However, as may be appreciated in FIG. 4, the concentration information for the drug to be administered may not be present in the dose order 400. In this regard, as was discussed in FIG. 3 with respect to method 300, a responsible caregiver may be prompted to provide the information corresponding to concentration information prior to generation of the configuration output. This request for additional information may be based on the configuration output generator 120 determining the parameter is not present in the dose order 400, yet included the configuration protocol of the infusion device 200. In this regard, it may be required that a responsible caregiver provide the information prior to the configuration output 500 being generated. In this case, the responsible caregiver may be an ordering physician, a pharmacist, a pharmacist technician, or other responsible caregiver capable of providing the information. For example, such information may be absent as the ordering caregiver may not be required to provide this information or may not be cognizant of the options for the concentrations of the specific drug that are available. For example, in this particular example the concentration of the drug may be determined by other factors such as the available stock in the pharmacy compounding the IV fluid 252, the method used to compound the IV fluid 252, or other factors such as the type of infusion device 220 to be used to administer the IV fluid 252. In another embodiment, the information corresponding to dose concentration 518 in the configuration output may be populated automatically during the compounding of the IV fluid 252 (e.g., a pharmacy work flow management system may be in operative communication with the configuration output generator 120 to automatically provide the information to the configuration output generator 120). In any regard, the drug concentration information 518 may be provided on the configuration output 500 so that the administering caregiver 130 may select the appropriate corresponding selection from the GUI 220 shown in FIG. 7D.

Figure 7E:
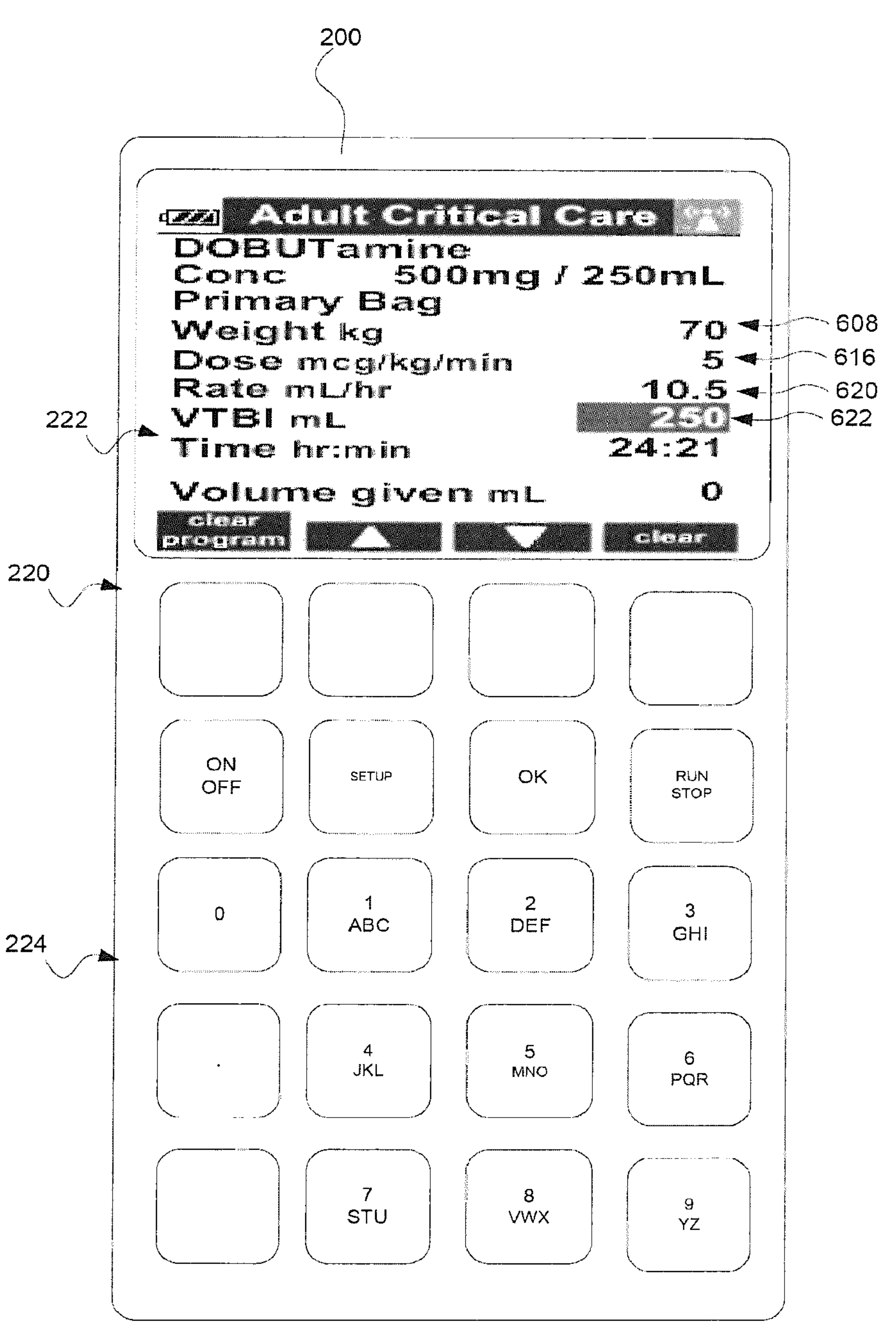

In this regard, the GUI 220 may change to the state shown in FIG. 7E (e.g., advancing the data input sequence of the configuration protocol) wherein the administering caregiver 130 may be prompted for configuration data components corresponding to patient weight 608, dose amount 616, dose administration rate 620, and volume to be infused (VTBI) 622. As may be appreciated, at least a part of the corresponding portions of data components (dose amount 616, dose administration rate 620, and VTBI 622) are provided in a corresponding order on the configuration output 500. However, it may be understood that because information corresponding to the patient weight 508 was not provided in the dose order 400, the patient weight 508 may have been received from a responsible caregiver (e.g., a doctor, nurse, or other caregiver) in a manner as described above. Alternatively, the information may be provided by an electronic medical records (EMR) server that includes the information. As such, the configuration output generator 120 may be in operative communication with a data store in which patient information is stored (e.g., an EMR server) and may be operable to automatically receive at least a portion of the data included in the configuration output 500.

In any regard, as may be appreciated from a collective review of the dose order 400 and the configuration output 500, the arrangement of the portions of the configuration output 500 corresponding to the values to be entered in FIG. 7E may be altered in arrangement from the dose order 400 to the configuration output 500. Additionally, the dose amount information 412 appearing in the dose order 400 appears in units of measure of micrograms per kilogram per hour. However, as may be appreciated in FIG. 7E, the configuration protocol for the infusion device 200 may prompt the administering caregiver 130 for this information in units of measure of micrograms per kilogram per minute. That is, there may be discrepancy in the units of measure used in the dose order 400 and the units of measure required for configuring the infusion device 200. As such, a unit conversion may be performed on the dose amount information 416 to modify the form of the dose amount information 516 of the configuration output by performing an appropriate unit conversion on the dose amount information 416.

As may be further appreciated, configuration data components for the rate 520 and VTBI 522 may not be present in the dose order 400. These values may be provided based on calculations employing other values present in the dose order 400 and/or the configuration output 500 and may be provided in an appropriate conforming form in the configuration output 500. For example, in the depicted embodiment, these values may be derived once the concentration of the drug 518 has been provided or obtained by the configuration output generator 120. It should be noted that the configuration or data components for the rate 520 and the VTBI 522 are presented in the appropriate order and the form (e.g., including units of measure) corresponding to the data input sequence of the configuration protocol of the infusion device 200.

In addition or alternatively to the foregoing description, another embodiment of a configuration output may include a code. As will be described in greater detail below, the use of a configuration output including a code may facilitate potential reduction of errors in configuring patient care devices. As such, with returning reference to FIG. 1, the configuration output generator 120 may be operable to generate a configuration output including a code as will be described in greater detail below. In this regard, any of the foregoing discussion generally relating to the generation of a configuration output (e.g., including the manner in which an order may be received, the manner in which the configuration output is generated or output, etc.) may be applicable to any of the embodiments presented below as was discussed above where applicable.

A code may be used to verify configuration data components entered by a user or may be indicative of configuration data components used to configure a patient care device. As such, embodiments directed to both approaches are discussed below. Also, in either regard, the code may be checked. That is, at least a portion of the code or a separate code (e.g., a check code) may be provided that may be used to validate a code that is entered by a user. As such, the code may be self-checking (e.g., include an integral check code) or a check code may be provided (e.g., distinct from the code or as a portion of the code such as, for example, at least one check digit).

Figure 8:
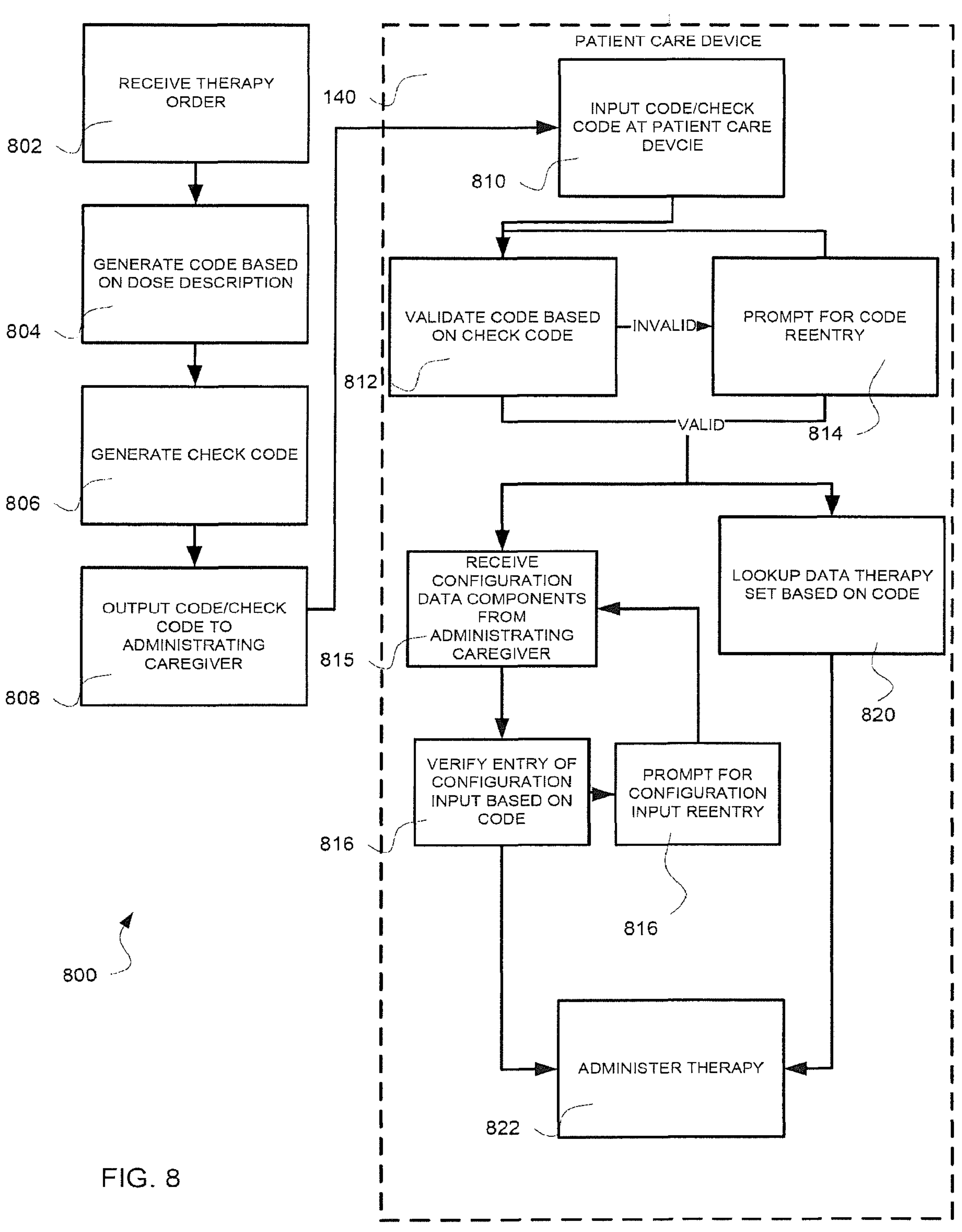
FIG. 8 depicts a flow chart corresponding to an embodiment of a method for generation and use of a code in the configuration of a patient care device.

Turning to FIG. 8, a flow chart depicts an embodiment of a process 800 for the generation of a configuration output including a code and for use of the code in the configuration of a patient care device. In this regard, the process 800 may be performed by one or more of the order entry interface 110 or configuration output generator 120 discussed above with respect to FIG. 1. That is, at least a portion of the process 800 may be performed in a computer-automated manner.

The process 800 may include receiving 802 a therapy order. In this regard, the receiving 802 may include any or all of the details associated with the order entry interface 110 discussed above. For example, in an embodiment, the therapy order received 802 may be a dose description 400 as shown and described above with respect to FIG. 4. That is, the therapy order received 802 may correspond with a dose order 400 that describes a therapy in the form of administration of an IV fluid 252 using an infusion device 200 (e.g., a configurable infusion pump). However, while the following description may refer to the dose order 400 for purposes of illustration, it may be appreciated that any type of order corresponding to any appropriate therapy to be administered by way of a configurable patient care device 140 (e.g., as discussed above) may be received 802.

The process 800 may also include generating 804 a code based on at least a portion of the therapy description (e.g., the dose description 400). For example, as described above, the dose order 400 may include one or more portions of information corresponding to one or more attributes of the IV fluid 252 to be administered or one or more attributes of the administration of the IV fluid. That is, the dose order 400 may include portions of information corresponding to an order number 402, an order date 404, a patient name 406, a drug name 410, a patient location 412, an ordering physician 414, and a dose amount 416. It may be appreciated that fewer or additional portions of information may be provided with a dose order 400 and that the specific portions shown in FIG. 4 are for explanation purposes and are not intended to be limiting. In this regard, one or more of the portions of the information of the dose description 400 (e.g., the portions of information corresponding to attributes of the IV fluid) may be utilized to generate the code.

In an embodiment, the generating 804 may include executing an algorithm to establish the code at least partially based on one or more portions of the dose description 400. As such, the one or more portions of the dose description 400 may include those portions of the dose description 400 to be verifiable by the code. It will be appreciated that in some instances, each portion of information from the dose order 400 to be used to configure the patient care device 140 may be verifiable by the code. However, in other instances, fewer than all portions of information to be used to configure the patient care device 140 may be verifiable by the code. In any regard, upon execution of the algorithm, the code may be generated (e.g., in a computer-animated manner). The resulting code may be repeatable by a corresponding algorithm that may be executed at a patient care device 140 or may be decipherable by the patient care device 140 as will be described in greater detail below. In an embodiment, the code resulting from execution of the algorithm may include one or more digits. The one or more digits may include printable ASCII characters (e.g., including letters, numbers, symbols, or other printable ASCII characters). In an embodiment, the code may include a plurality of alphanumeric digits.

Furthermore, the process 800 may optionally include generating 806 a check code. As referenced above, a check code may be provided that is separate from, as a portion of, or may form an integral part of the code generated at 804. The check code 806 may include one or more digits that are at least partially based on the one or more digits of the code generated at 804. As such, upon entry of a code and a check code, the check code may be used to validate the code that is entered to be determine if the code is valid (e.g., that the code was entered correctly by the administering caregiver). Accordingly, errors in entry of the code (e.g., transcription errors when entering the code) may be detectable such that rectification of the error may be addressed prior to the administration of the therapy.

A check code may be generated using any one or more of a plurality of algorithms capable of generating at least one check digit based on the content of a base code. Examples of possible algorithms include Mod-10, Mod-11, ISO 2894/ANSI 4.13, or JTC1/SC 17 codes. Any other appropriate method or algorithm known in the art may also be utilized. The algorithm for generation of a check code may form a part of a code or generate one or more check digits that may provide a "pass/fail" designator for an entered code. Additionally the algorithm may include more sophisticated indications of the status of a code. For example, depending on the approach used to generate the check code and/or the approach used to validate the code using the check code, additional information such as the type of error, the location of the error, or other valuable information about the entered code may be determined.

In any regard, the process 800 may include outputting 808 the code and check code. For example, the outputting 808 may include the code and check code with a configuration output. As such, the configuration output including the code and check code may be output in any manner as described above (e.g., printing a hardcopy label, displaying the configuration output as a soft copy, etc.). In any regard, the outputting of the 808 code and check code may include distributing the configuration output to an administrating care giver 130 for use in configuration of a patient care device 140.

Accordingly, the process 800 may further include inputting 810 a code and, if used, a check code at the patient care device 140. In this regard, the inputting 810 may include transcribing the code and check code into the patient care device 140 using, for example, a graphical user interface 220 as described above. As such, the inputting 810 may include the administrating caregiver 130 manually entering the code and check code at the patient care device 140 (e.g., as transcribed from the configuration output).

If a check code is utilized, upon the inputting 810 of the code and check code at the patient care device 140, the process 800 may include validating 812 the entered code based on the check code. As described above, the validating 812 may include execution of a corresponding algorithm at the patient care device 140 with respect to the code to generate a corresponding check code. Upon determining the corresponding check code for an entered code, the validating 812 may include comparison of the determined corresponding check code to the entered check code to determine if the determined corresponding check code and entered check code correspond. Alternatively, the validating 812 may include executing a corresponding, but different, algorithm as compared to the algorithm used to generate the check code. In this regard, the corresponding algorithm may be operable to decipher the entered code and/or entered check code to determine if the code that was entered was in fact entered correctly (i.e., was a valid code/check code combination of the generating algorithm). In this regard, any approach to the use of algorithms for validating 812 codes with the use of a check code may be executed without limitation.

In the event that an invalid code is determined in the validating 812, the process 800 may include prompting 814 for reentry of the code and/or check code. Upon reentry of the code and/or check code in response of the prompting 814, the process 812 may again include validating 812 the reentered code. This may continue until a valid code has been entered.

The process 800 may include multiple embodiments of manners in which the code may be used. In this regard, either or both of the approaches outlined below (corresponding to configuration data component validation or configuration data component indication) may be used separately or collectively in various embodiments of the process 800.

Accordingly, in an embodiment, the process 800 may include verifying 816 entry of one or more input configuration data components that are received at the patient care device 140 (e.g., transcribed by an administrating caregiver 130). In this regard, the administrating caregiver 130 may enter one or more configuration data components (e.g., from the configuration output) for configuration of the patient care device 140. In turn, the code and/or check code entered at 818 may be used to verify 814 the one or more entered configuration data components. Accordingly, the patient care device 140 may include a verification algorithm that corresponds to the algorithm used in generating 804 the code. The corresponding verification algorithm may be a copy of the algorithm used in the generating 804 of the code such that the entered configuration data components are used as inputs to the algorithm at the patient care device 140 and the resulting code is compared to the entered code. Alternatively, the corresponding algorithm may be capable of deciphering the entered code to provide a plurality of values (e.g., expected configuration data component values) that are compared to entered configuration data components to verify the entered configuration data components.

In this regard, in the event the verifying 816 indicates that one or more of the configuration data components are incorrect the process 800 may include prompting 818 for reentry of one or more of the configuration data components and/or the code. Otherwise, the process 800 may continue and the therapy may be administered 822 by the patient care device 140 as configured by the entered configuration data components.

In another embodiment of the process 800, the code may be indicative of one or more configuration data components for use in configuring the patient care device 140. In this regard, the entry of the code may be used to configure the patient care device 140 in lieu of manual entry of one or more corresponding configuration data components. For example, the patient care device 140 may be provided with logic (e.g., prior to receipt of the code) to decipher an inputted code that is indicative of one or more configuration data components. The patient care device may utilize the deciphered information from the code to obtain configuration data components for use in configuring the patient care device for administration of the therapy to a patient.

In an implementation, the deciphered information may indicate pre-stored therapy data that is to be used to configure the patient care device for administration of the therapy. That is, the code may indicate a portion of a pre-stored therapy data set that may be accessed based on the code that is entered. As will be discussed in greater detail below, the code may include an indication of a portion of a master drug library (MDL) stored at or accessed by the patient care device 140. In this regard, the code may be used to locate an appropriate entry in the MDL that may include one or more configuration data components for use in configuring the patient care device 140. As such, upon entry of the code and retrieval of the configuration data components from the pre-stored therapy data set based on the code, the process 800 may include administration 822 of the therapy as at least partially based on the retrieved configuration data components.

In an implementation, the deciphered information from the code may itself comprise one or more configuration data components for use in configuring the patient care device. That is, upon deciphering the code, the patient care device 140 may be able to determine configuration data components that were encoded by the entered code.

In either regard, the provided logic may include an appropriate algorithm at the patient care device to decipher the inputted code. That is, the patient care device may be provided with such logic prior to receipt of the code in order to perform the functionality associated with deciphering the code. Accordingly, for example, in the implementation where configuration data components may be deciphered directly from the code, a pre-configured patient care device including the corresponding algorithm may obtain the configuration data components even in the absence of a pre-stored therapy data set.

As may be appreciated either or both of the foregoing approaches may be used. That is, a code that verifies entered configuration data components and/or a code that is indicative of configuration data components may be provided. In the event both approaches are facilitated, the verified and indicated configuration data components may overlap such that at least some of the configuration data components are both indicated by the code and verified by the code. Additionally or alternatively, some configuration data components may be verified by the code and others of the configuration data components may be indicated by the code.

In some embodiments, the patient care device 140 may be provided with logic and/or otherwise configurable to determine whether or not the input of one or more code(s), as may be generated and/or provided in a configuration output described herein, is required to configure or otherwise enable the patient care device 140 for a given intended operation (e.g., an administration procedure). For example, the patient care device 140 may be configured so that in certain predeterminable uses code input is required while in other predeterminable uses code input is not required.

Figure 9:
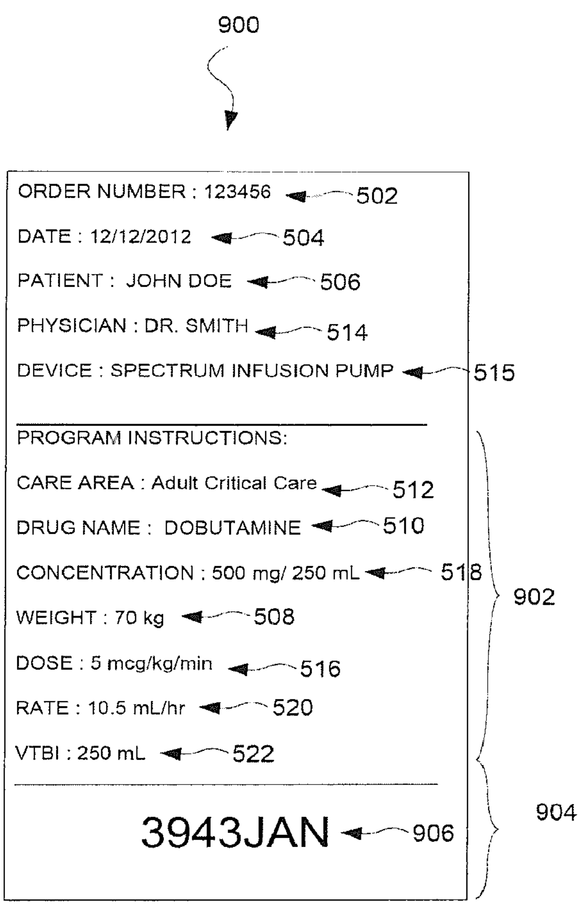
FIG. 9 depicts an embodiment of a configuration output that includes one or more plain text values corresponding to the dose description of FIG. 4 and a code for verification of configuration data component inputs corresponding to at least a portion of the dose description.
Figure 10:
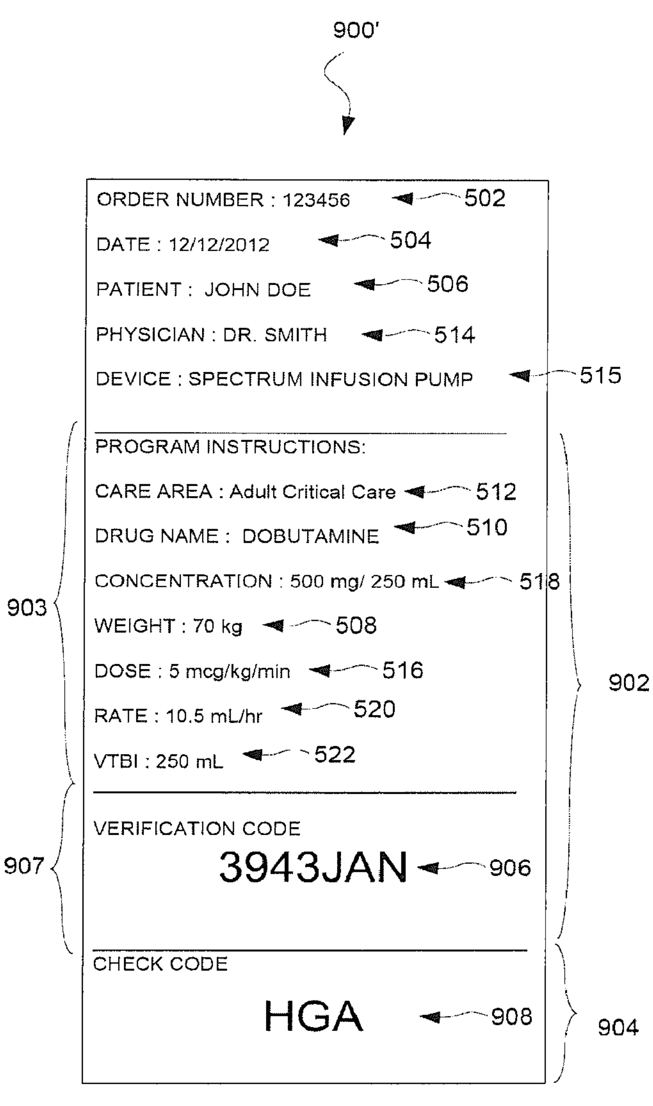
FIG. 10 depicts an embodiment of a configuration output with one or more plain text values corresponding to the dose description of FIG. 4, a code for verification of configuration data component inputs corresponding to at least a portion of the dose description, and a check code for validation of the verification code.
Figure 13:
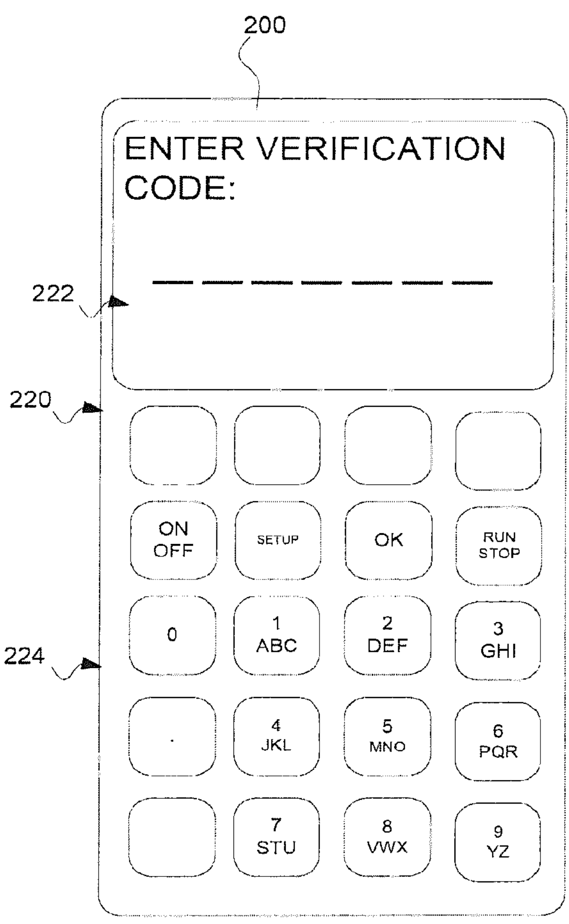
FIG. 13 depicts an embodiment of a graphical user interface of a configurable infusion device in a state for receiving a code from a configuration output.

In view of the foregoing, FIGS. 9-11 depict different examples that generally correspond to examples of configuration outputs with at least one code for use in configuration of a patient care device according to at least one of the embodiments described above with respect to FIG. 8. FIGS. 9-11 each generally correspond to various configuration outputs generated based on the dose order 400 shown in FIG. 4. However, it may be appreciated that the features discussed in FIGS. 9-11 may be generally applicable to any therapy order for configuration of any kind of patient care device 130 as described herein.

With respect to FIG. 9, the configuration output 900 may include a first portion 902. The first portion 902 may, as can be appreciated in FIG. 9, be at least partially generated based on a portion of the dose description 400. For instance, the first portion 902 may include portions of configuration data 508-512 and 518-522 as described above in FIG. 5. In this regard, it may be appreciated that the first portion 902 of the configuration output 900 may include plain text values corresponding to configuration data components that are based on the dose description 400. For example, as shown, the first portion 902 may include one or more exact values from the dose description 400.

Furthermore, in an embodiment, the plain text values may be patient care device-specific data presented in accord with the foregoing description related to a patient care device-specific configuration output based at least in part on at least a portion of each of a corresponding therapy description and the predetermined configuration protocol of an identified patient care device 140. However, it may also be appreciated that the first portion 902 may present the configuration data that is based on the dose description 400 in any other appropriate manner and is not required to incorporate the teachings described above.

The configuration output 900 may include a second portion 904. The second portion 904 may include a code 906. The code 906 may be based on one or more of the value of the configuration data 902 in the first portion 902. In this regard, the code 906 may be a first code in configuration output 900 because it is at least partially generated based on the first portion 902. In this regard, the code 906 may, as described above, be generated by applying an algorithm to one or more of the configuration data components presented in the first portion 902. In this regard, the first portion 902 may be based upon the dose description 400 as well as a configuration protocol of a configurable patient care device 140 (e.g., a configurable infusion pump). In any regard, the code 906 may be based upon the first portion 902 such that the code 906 may be used to verify the correct entry (e.g., transcription) of one or more entered configuration data components from the first portion 902.

In an embodiment, the first portion 902 may include configuration data corresponding to each data component of a configuration protocol for a patient care device 140. As such, the code 906 may be operable to verify the correct entry of all the components of the configuration data to be input at the patient care device 140. As described above, this may include performing a corresponding algorithm at the patient care device 130 to independently generate a code that is compared to the entered code or may include deciphering of an entered code to verify the entered code corresponds to the configuration data of the first portion 902.

In an embodiment of a configuration output 900' depicted in FIG. 10, the configuration output 900' may also include a check code 908. In this regard, the configuration output 900' may include a first portion 902. The first portion 902 may include a first part 903. The first part 903 may include plain text values corresponding to the dose description 400 and/or a configuration protocol of a patient care device as described above with respect to the configuration output 900 of FIG. 9. The first portion 902 may also include a second part 907 that includes a code 906. The code 906 may be a second code in configuration output 900' because it is at least partially based on a portion of the therapy description (e.g., the dose order 400). That is, the code 906 may be based upon the values of the first part 903. As such, the code 906 may be used at the configuration device to verify the correct entry of one or more of the configuration data from the first part 903 as described above.

The configuration output 900' may also include a second portion 904. The second portion 904 may also include another code, e.g. a check code 908. The check code 908 may be a first code in the configuration output 900' because it is at least partially generated based on the first portion 902. Namely, the check code 908 may be at least partially generated based on the code 906 used to verify the correct entry of the configuration data components of the first portion 902. That is, the check code 908 may be generated based on the code 906 of the first portion 902. In this regard, the administrating care giver 130 may enter at the patient care device 140 one or more values from the plain text values of the first part 902. The administrating care giver 130 may also enter at the patient care device 140 the code 906 and the check code 908. Accordingly, the patient care device 140 may be operable to verify the entered configuration data values based on the code 906. Furthermore, the code 906 may be validated based on the check code 908 by checking the code 906 in relation to the check code 908. While a separate check code 908 is shown in FIG. 10, it may be appreciated that the check code 908 may be provided as one or more additional digits of the code 906 and/or integral to one or more digits of the code 906.

With further reference to FIG. 11, an embodiment of a configuration output 900" is shown. The configuration output 900" may include a first portion 902. The first portion 902 may include at least a portion of a code 906 that is at least partially based on the dose order 400. In this regard, the code 906 may be a second code in configuration output 900" because it is at least partially generated based on the therapy description (e.g., the dose order 400). For example, the first portion 902 may be generated upon execution of an algorithm applied to one or more information values from the dose order 400 as described above. The configuration output 900" may include a second portion 904 that is at least partially based on the first portion 902. For example, the second portion 904 may include a check code 908 (e.g., comprising at least one digit of the code 906) generated based on the code portion of the first portion 902. In this regard, the check code 908 may be a first code in configuration output 900" because it is at least partially generated based on the first portion 902. That is, the check code 908 may be at least partially generated based on the second code 906 of the first portion 902 of the configuration output 900". As such, the second portion 904 may be used to validate the code 906 including the first and second portions 902 and 904. It may be appreciated that the configuration output 900" may not include plain text values corresponding to configuration data components. As such, in the configuration output 900" shown in FIG. 11, the first portion 902 may be indicative of one or more configuration data components. That is, rather than entry of configuration data components by the administering caregiver 130, the administrating caregiver 130 may enter the code 906 (e.g., including the first portion 902 and the second portion 904). As described above, the second portion 904 (e.g., the check code) may be used to validate the first portion 902. In turn, the first portion 902 may indicate to the patient care device 140 one or more configuration data components to be used to configure the patient care device 140 in order to administer the therapy according to the therapy order (e.g., to administer the IV fluid 252 described in the dose order 400). In this regard, the one or more configuration data components may be retrieved from a pre-stored therapy set that is accessible by the patient care device 140.

For example, the patient care device 140 may have access to a master drug library MDL 1200 (e.g., as shown in FIG. 12). The MDL 1200 may be stored locally in memory at the patient care device 140, or the MDL 1200 may be accessed by the patient care device 140 by way of a network (e.g., a local area network, a wide area network, a wireless network, etc.). In any regard, the MDL 1200 may include a plurality of rows 1202. Each of the rows 1202 (e.g., row 00-row N) may include one or more configuration data components. For example, as shown, each row may include data corresponding to a care area 1212, a drug to be administered 1210, a concentration 1218, a dose 1216, a rate 1220, and a VTBI 1222. In this regard, it may be appreciated that at least some of the configuration data components to be used to configure the patient care device 140 may be provided in each corresponding one of the rows 1202. As such, the code 906 may be interpretable by the patient care device 140 as an indicator to a row 1202 in the MDL 1200. For example, with reference to the dose description 400, the code 906 of the configuration output 900" may indicate to the patient care device 140 that row 46 (as indicated by arrow 1204 in FIG. 12) of the MDL 1200 should be used such that one or more appropriate configuration data components are returned from row 46 in order to configure the patient care device 140.

As may be appreciated, some configuration data components may be dependent upon received data (e.g., patient weight). In this regard, the values for rate 1220 and VTBI 1222 (which may be related to patient weight) may not be explicit values in the rows 1202 of the MDL 1200. As such, in an implementation the values for rate 1220 and VTBI 1222 may be requested from the administering caregiver 130. Alternatively or additionally, a related value (e.g., patient weight) may be requested from the administering caregiver 130 such that the values for rate 1220 and VTBI 1222 are automatically calculated. In this regard, the fields for rate 1220 and VTBI 1222 may include formulas based on one or more other values (e.g., patient weight, etc.) Furthermore, in addition to specific values or formulas, a row 1202 in the MDL 1200 may include acceptable ranges (e.g., for rate 1220 and VTBI 1222) that may be used to determine if an entered value is within the acceptable range.

With returning reference to FIG. 8, a code used to verify and/or indicate one or more configuration data components may be one of a plurality of predeterminable codes that may be generated in the generating 804 step of the process 800. That is, for example, in an embodiment where an algorithm is used in the generating 804, the algorithm may be operable to generate a plurality of different codes. These different codes may correspond to identical inputs. For example, even if two identical therapy orders are received (e.g., to be administered to two different patients), the generating 804 may include generating different codes for the identical therapy orders. In this regard, as will be discussed in greater detail below, the different ones of the plurality of predeterminable codes may be used at least in part to track or maintain records related to therapy orders.

For example, in an embodiment, each one of the plurality of predeterminable codes may be generable in corresponding relation to a different one of a plurality of time periods. That is, continuing the example of an algorithm used in the generating 804, the algorithm may be operable to produce a plurality of different predeterminable codes (e.g., even for identical inputs) in one of the plurality of time periods. Each one of these plurality of predeterminable codes may correspond to a different one of a plurality of time periods. For example, for a given time period, a given one of the plurality of codes may be generated only once during the time period. The determination of the time period may be based on a given temporal period (e.g., 2 hours, 4 hours, 8 hours, etc.) or may be based on the occurrence of a number of doses (e.g., 5,000 doses, 10,000 doses, 20,000 doses, etc.). Furthermore, the basis of the different time periods may differ between different ones of the time periods (e.g., some time periods may be based on a temporal period while others may be based on a number of doses). Regardless of the basis of the different time periods, each code generated during any given time period may be unique.

As such, during a time period, the code may be used to track a corresponding therapy order. For instance, upon entry of a code at a patient care device, the patient care device may be operable to communicate receipt of the code for storage in corresponding relation with other parameters. These other parameters may include, for example, identification information for the patient care device, patient information, location information, etc. As such, by communicating the receipt of the code along with, for example, patient care device information, the code may be used to correlate the identity of the patient, details of the therapy, and the patient care device used to administer the therapy. For example, this may include storing information in a database that may be stored locally or remotely from the patient care device. In an embodiment, the database may comprise a medical records database (e.g., an electronic medical records (EMR)) database.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A configuration output generator apparatus comprising:
- a processor; and
- a memory including non-transitory machine-readable instructions, which when executed, cause the processor to:
  - receive a therapy order that includes a therapy description corresponding to a therapy to be administered by a patient care device to a patient,
  - generate a first portion of a configuration output from the therapy order, the first portion of the configuration output including plain text values specifying a configuration protocol for performing the therapy,
  - generate, using an algorithm and the first portion of the configuration output, a second portion of the configuration output that comprises an alphanumeric code, and
  - output the first portion of the configuration output and the second portion of the configuration output for entry into the patient care device,
  - wherein the second portion of the configuration output is configured for use by the patient care device to confirm the first portion of the configuration output was correctly input into the patient care device, thereby enabling the patient care device to administer the therapy according to at least the first portion of the configuration output, and
  - wherein the first portion of the configuration output at least partially corresponds to one or more components of the therapy order, a data input sequence of the configuration protocol, or at least one configuration parameter of the configuration protocol.

2. The configuration output generator apparatus of claim 1, wherein the therapy order includes a dose order specifying a dose description corresponding to an intravenous fluid to be administered using the patient care device.

3. The configuration output generator apparatus of claim 2, wherein outputting the first portion of the configuration output and second portion of the configuration output includes causing a printer to print a label that is attached to a container of the intravenous fluid to be administered using the patient care device.

4. The configuration output generator apparatus of claim 1, wherein outputting the first portion of the configuration output and second portion of the configuration output includes displaying the first portion of the configuration output and second portion of the configuration output as a soft copy.

5. The configuration output generator apparatus of claim 1, wherein the therapy order includes at least an order number, an order date, a patient name or identifier, a drug name, a patient location, and a dose amount.

6. The configuration output generator apparatus of claim 1, wherein the memory includes further non-transitory machine-readable instructions, which when executed, cause the processor to generate a check code using the second portion of the configuration output.

7. The configuration output generator apparatus of claim 6, wherein the check code is generated using a second algorithm that includes at least one of a Mod-10 algorithm, a Mod-11 algorithm, an ISO 2894/ANSI 4.13 algorithm, or a JTC1/SC 17 algorithm.

8. The configuration output generator apparatus of claim 1, wherein the patient care device includes at least one of an infusion device, a patient monitor, an inhalation therapy device, an enteral feeding pump, a respiratory ventilation device, or a dialysis device.

9. The configuration output generator apparatus of claim 1, wherein the therapy order includes at least one of a care area, an intravenous fluid name, a concentration of the intravenous fluid, a patient weight, a dose of the intravenous fluid, an infusion rate of the intravenous fluid, or a volume to be infused of the intravenous fluid.

10. A configuration output generator apparatus comprising:
- a processor; and
- a memory including non-transitory machine-readable instructions, which when executed, cause the processor to:
  - receive a therapy order corresponding to an infusion therapy to be administered by an infusion pump,
  - generate a first portion of a configuration output from the therapy order, the first portion of the configuration output including plain text values specifying a configuration protocol for performing the infusion therapy,
  - generate, using an algorithm and the first portion of the configuration output, a second portion of the configuration output that comprises an alphanumeric code, and output the first portion of the configuration output and the second portion of the configuration output for entry into the infusion pump, wherein the second portion of the configuration output is configured for use by the infusion pump to confirm the first portion of the configuration output was correctly input into the infusion pump, thereby enabling the infusion pump to administer the infusion therapy according to at least the first portion of the configuration output, and wherein the first portion of the configuration output at least partially corresponds to one or more components of the therapy order, a data input sequence of the configuration protocol, or at least one configuration parameter of the configuration protocol.

11. The configuration output generator apparatus of claim 10, wherein the therapy order includes at least one of a care area, an intravenous fluid name, a concentration of the intravenous fluid, a patient weight, a dose of the intravenous fluid, an infusion rate of the intravenous fluid, or a volume to be infused of the intravenous fluid.

12. The configuration output generator apparatus of claim 10, wherein the memory includes further non-transitory machine-readable instructions, which when executed, cause the processor to generate a check code using the second portion of the configuration output.

13. The configuration output generator apparatus of claim 12, wherein the check code is generated using a second algorithm that includes at least one of a Mod-10 algorithm, a Mod-11 algorithm, an ISO 2894/ANSI 4.13 algorithm, or a JTC1/SC 17 algorithm.

14. The configuration output generator apparatus of claim 10, wherein outputting the first portion of the configuration output and second portion of the configuration output includes causing a printer to print a label that is attached to a container of an intravenous fluid to be administered using the infusion pump.

15. The configuration output generator apparatus of claim 10, wherein outputting the first portion of the configuration output and second portion of the configuration output includes displaying the first portion of the configuration output and second portion of the configuration output as a soft copy.

16. The configuration output generator apparatus of claim 10, wherein the therapy order is received from an order entry interface.

* * * * *